(12) United States Patent
Gronborg et al.

(10) Patent No.: US 7,595,336 B2
(45) Date of Patent: Sep. 29, 2009

(54) ISATINE DERIVATIVES WITH NEUROTROPHIC ACTIVITY

(75) Inventors: Mette Gronborg, Kobenhavn NV. (DK); Dan Peters, Malmo (SE); Arne Moller, Sjaellands Odde (DK)

(73) Assignee: Neurosearch A/S, Ballerup (DK)

(*) Notice: Subject to any disclaimer, the term of this patent is extended or adjusted under 35 U.S.C. 154(b) by 228 days.

(21) Appl. No.: 11/453,892

(22) Filed: Jun. 16, 2006

(65) Prior Publication Data

US 2006/0229311 A1    Oct. 12, 2006

Related U.S. Application Data

(62) Division of application No. 10/169,415, filed on Jul. 1, 2002, now Pat. No. 7,282,511.

(51) Int. Cl.
*A61K 31/40* (2006.01)
*C07D 209/56* (2006.01)

(52) U.S. Cl. .................. 514/411; 548/427
(58) Field of Classification Search ............. 514/411; 548/427, 416
See application file for complete search history.

(56) References Cited

U.S. PATENT DOCUMENTS

| 4,322,533 | A | | 3/1982 | Lesher et al. | |
| 5,801,174 | A | * | 9/1998 | Moldt et al. | 514/250 |
| 5,843,945 | A | * | 12/1998 | Watjen et al. | 514/250 |
| 5,917,053 | A | * | 6/1999 | Moldt et al. | 548/433 |
| 6,693,111 | B1 | * | 2/2004 | Watjen et al. | 514/292 |
| 7,288,653 | B2 | * | 10/2007 | Varming et al. | 546/84 |

FOREIGN PATENT DOCUMENTS

| EP | 0 432 648 A2 | 6/1991 |
| EP | 0 529 636 A1 | 3/1993 |
| EP | 0 089 394 A1 | 8/1993 |
| EP | 0 556 393 A1 | 8/1993 |
| EP | 0 572 852 A1 | 12/1993 |
| EP | 0 919 554 A1 | 6/1999 |
| EP | 1 002 535 A1 | 5/2000 |
| JP | 6-228112 A1 | 8/1994 |
| WO | WO-94/26747 A1 | 11/1994 |
| WO | WO-96/08494 A1 | 3/1996 |
| WO | WO-96/08495 A1 | 3/1996 |
| WO | WO-96/11922 A1 | 4/1996 |
| WO | WO-96/12724 A1 | 5/1996 |
| WO | WO-98/14447 A | 4/1998 |
| WO | WO-99/49864 A1 | 10/1999 |
| WO | WO-00/01376 A2 | 1/2000 |
| WO | WO-00/71102 A2 | 5/2000 |
| WO | WO-00/33834 A1 | 6/2000 |

OTHER PUBLICATIONS

Hesson et al., Bioorganic & Medicinal Chemistry Letters, vol. 7, No. 11, pp. 1437-1442 (1997).
J. Pharmacol Exp Ther, vol. 289, No. 3, pp. 1492-1501 (1999) (Abstract).
Jensen et al., Neurochem. Int., vol. 32, pp. 505-513 (1998).
Ohmori et al., J. Med. Chem., vol. 39, pp. 3971-3979 (1996).
Ohmori et al., J. Med. Chem. vol. 39, pp. 1331-1338 (1996).
Winkler et al., Pharmacology and Pathophysiology, CNS Drugs, vol. 2, No. 6, pp. 466-478 (1994).
Science, vol. 264, pp. 772-774 (1994).
Pechan et al., NeuroReport, vol. 6, pp. 669-672 (1995).

* cited by examiner

*Primary Examiner*—James O. Wilson
*Assistant Examiner*—Paul V. Ward
(74) *Attorney, Agent, or Firm*—Birch, Stewart, Kolasch & Birch, LLP

(57) ABSTRACT

The present invention relates to novel isatin derivatives, pharmaceutical compositions comprising the isatin derivatives of the invention, methods of preparing the isatin derivatives of the invention, their use in the treatment of neurodegenerative diseases and for the regeneration or prevention of degeneration of lesioned and damaged neurons, and methods of treatment of neurodegenerative diseases and for the regeneration or prevention of degeneration of lesioned and damaged neurons.

8 Claims, 6 Drawing Sheets

ISATINE DERIVATIVES WITH NEUROTROPHIC ACTIVITY

CROSS-REFERENCE TO RELATED APPLICATIONS

The present application is a 37 C.F.R. § 1.53(b) divisional of U.S. application Ser. No. 10/169,415 filed Jul. 1, 2002, now U.S. Pat. No. 7,282,511, which in turn claims priority on Danish Application No. PA 2000 00106 filed Jan. 24, 2000. The entire contents of each of these applications is hereby incorporated by reference.

TECHNICAL FIELD

The present invention relates to novel isatin derivatives, pharmaceutical compositions comprising the isatin derivatives of the invention, methods of preparing the isatin derivatives of the invention, their use in the treatment of neurodegenerative diseases and for the regeneration or prevention of degeneration of lesioned and damaged neurons, and methods of treatment of neurodegenerative diseases and for the regeneration or prevention of degeneration of lesioned and damaged neurons.

BACKGROUND ART

Growth factors (or neurotrophic factors) promote the differentiation, growth and survival of numerous peripheral and central nervous system neurons during development and adulthood. The molecular characteristics, regulation and signal transduction mechanism for a number of neurotrophic factors have been identified. The most therapeutically promising of these molecules are nerve growth factor (NGF), brain-derived neurotrophic factor (BNDF), ciliary neurotrophic factor (CNTF), basic fibroblast growth factor (bFGF), insulin-like growth factor-I (IGF-1), and glial cell-line derived neurotrophic factor (GDNF).

Available data suggests that neurotrophic factors will be useful in the treatment of neurodegenerative diseases such as Alzheimer's disease, Parkinson's disease and amyotrophic lateral sclerosis. Additionally neurotrophic factors have shown beneficial effects in animal models of peripheral nerve damage and toxin induced neuropathy [*CNS Drugs* 1994 2 (6) 465-478].

Various rat studies predict that compounds mimicking or enhancing the function of NGF can rescue septal cholinergic neurons and alleviate benign forgetfulness and the memory impairment seen in senile dementia [*Science* 1994 264 772-774].

Recent studies have shown that NGF has a neuro protective effect on hippocampal neurons after cerebral ischaemia, which predicts a potential therapeutic role for NGF in the treatment of cerebral ischaemic neuronal damage [*NeuroReport* 1995 6 (4) 669-672].

Growth factors initiate their biological action by binding to specific cell surface receptors. Binding of the growth factor to its receptor activates the intracellular signal transduction, leading to the generation of various second messengers and activation of enzyme cascades, involving tyrosine kinases and protein kinase C, and culminates in a biological effect. The intracellular signal transduction pathway is not yet fully understood.

NGF and related neurotrophins are large peptides, which makes them unlikely therapeutic candidates. Poor pharmacokinetic parameters (e.g. poor oral absorption and short in vivo half life), and administration to the target organs represent the major problems.

There is a continued need for the development of new compounds capable of interacting with the neurotrophin-receptors, and which shows physicochemical properties different from the neurotrophins.

SUMMARY OF THE INVENTION

According to the present invention new neutrophically active compounds are provided. The neurotrophic activity has not been ascribed to a specific step in the interaction between NGF and its receptor or in the NGF signal transduction pathway.

The neurotrophic activity of the compounds of the invention makes them useful for the treatment or prevention of various degenerative diseases of the nerves, including Alzheimer's disease, Parkinson's disease, Huntington's disease, and amyotrophic lateral sclerosis (ALS), and for the alleviation of benign forgetfulness and the memory impairment seen in senile dementia or in connection with neurodegenerative diseases.

Moreover, the compounds of the invention have shown to be useful for the treatment of neuropathy and in particular peripheral neuropathy caused by e.g. genetic abnormalities and other conditions such as diabetes, polio, herpes and AIDS, and most especially neuropathy and peripheral neuropathy experienced by most cancer patients after or during chemotherapy.

The compounds of the present invention are considered to be particularly useful for the treatment of traumatic lesions of peripheral nerves, the medulla, and/or the spinal cord, and in the treatment of cerebral ischaemia, e.g. ischaemic neuronal damage following cardiac arrest, stroke, or postasphyxial brain damage in new-borns, or following near-drowning.

In its first aspect the invention provides novel isatin derivatives represented by the general formula (I)

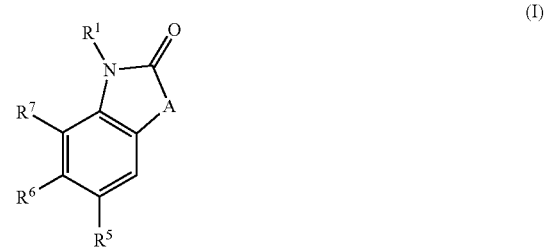

or a pharmaceutically acceptable salt thereof, wherein,

A represents a group of the formula —C(NOR$^2$)— or —NR$^2$—CO—;

R$^1$ represents hydrogen or an alkyl group;

R$^2$ represents hydrogen, an alkyl group, an acyl group, an oxo-tetrahydrofuryl group, an isoxazolyl-alkyl group, or an isoxazolyl group, which alkyl group may optionally be substituted with one or more hydroxy or carboxy, and which isoxazolyl group may optionally be substituted with one or more substituents selected from the group consisting of alkyl or alkoxy;

R$^5$ represents a phenyl group, a benzyl group, or a 5 or 6-membered monocyclic heterocyclic group, which groups may optionally be substituted one or more times with halogen, CF$_3$, —OCF$_3$, NO$_2$, amino, aminosulfonyl, alkyl, alkoxy, alkoxycarbonyl, or phenyl;

$R^6$ and $R^7$ together form a fused 5 to 7 membered ring composed by one of the following bridging bivalent radicals (read in the direction $R^6$ to $R^7$):
—$CH_2$—$CH_2$—
—$CH_2$—$CH_2$—$CH_2$—;
—$NR^{12}$—$CH_2$—$CH_2$—;
—$CH_2$—$CH_2$—$NR^{12}$—;
—$CH_2$—$NR^{12}$—$CH_2$—;
—$NR^{12}$—$CH_2$—$NR^{12}$—;
—$CH_2$—$CH_2$—$CH_2$—$CH_2$—;
$CH_2$—$CH_2$—$NR^{12}$—$CH_2$—;
—$CH_2$—$NR^{12}CH_2$—$CH_2$—;
—$CH_2$—$CH_2$—$CH_2$—$NR^{12}$—;
—$NR^{12}$—$CH_2$—$CH_2$—$CH_2$—;
—$NR^{12}$—$CH_2$—$CH_2$—$NR^{12}$—;
—$CH_2$—$CH_2$—$CH_2$—$CH_2$—$CH_2$—;
—$CH_2$—$CH_2$—$NR^{12}$—$CH_2$—$CH_2$—;
—$CH_2$—$CH_2$—$CH_2$—$NR^{12}CH_2$—;
—$CH_2$—$NR^{12}CH_2$—$CH_2$—$CH_2$—$CH_2$—;
—$CH_2$—$CH_2$—$CH_2$—$CH_2$—$NR^{12}$—; or
—$NR^{12}$—$CH_2$—$CH_2$—$CH_2$—$CH_2$—;

wherein $R^{12}$ represents hydrogen, a group of the formula —$CH_2CH_2OH$, —$CO$—$CH_3$, —$SO_2$—$CH_3$, or an alkyl group;

or $R^6$ and $R^7$ independently of each other represent hydrogen or methyl.

In another aspect the invention provides pharmaceutical compositions comprising a therapeutically-effective amount of a compound of the invention together with at least one pharmaceutically-acceptable carrier or diluent.

In a third aspect the invention relates to the use of a compound of the invention for the manufacture of a medicament for the treatment or alleviation of a disease or a disorder or a condition of a mammal, including a human, which disease or disorder or condition is responsive to the activity of a neurotrophic agent.

In a fourth aspect the invention provides a method for treatment or alleviation of a disease or a disorder or a condition of a mammal, including a human, which disease or disorder or condition is responsive to the activity of a neurotrophic agent, which method comprises administering to said mammal in need thereof an effective amount of a compound of the invention.

Other objects of the invention will be apparent to the person skilled in the art from the following detailed description and examples.

DETAILED DISCLOSURE OF THE INVENTION

Novel Neutrophic Compounds
In its first aspect the invention provides novel isatin derivatives of the general formula (I)

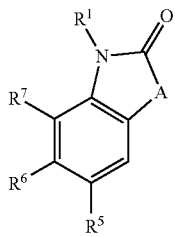

(I)

or a pharmaceutically acceptable salt thereof, wherein,
A represents a group of the formula —$C(NOR^2)$— or —$NR^2$—$CO$—;
$R^1$ represents hydrogen or an alkyl group;
$R^2$ represents hydrogen, an alkyl group, an acyl group, an oxo-tetrahydrofuryl group, an isoxazolyl-alkyl group, or an isoxazolyl group, which alkyl group may optionally be substituted with one or more hydroxy or carboxy, and which isoxazolyl group may optionally be substituted with one or more substituents selected from the group consisting of alkyl or alkoxy;

$R^5$ represents a phenyl group, a benzyl group, or a 5 or 6-membered monocyclic heterocyclic group, which groups may optionally be substituted one or more times with halogen, $CF_3$, —$OCF_3$, $NO_2$, amino, aminosulfonyl, alkyl, alkoxy, alkoxycarbonyl, or phenyl;

$R^6$ and $R^7$ together form a fused 5 to 7 membered ring composed by one of the following bridging bivalent radicals (read in the direction $R^6$ to $R^7$):
—$CH_2$—$CH_2$—
—$CH_2$—$CH_2$—$CH_2$—;
—$NR^{12}$—$CH_2$—$CH_2$—;
—$CH_2$—$CH_2$—$NR^{12}$—;
—$CH_2$—$NR^{12}$—$CH_2$—;
—$NR^{12}$—$CH_2$—$NR^{12}$—;
—$CH_2$—$CH_2$—$CH_2$—$CH_2$—;
—$CH_2$—$CH_2$—$NR^{12}$—$CH_2$—;
—$CH_2$—$NR^{12}$—$CH_2$—$CH_2$—;
—$CH_2$—$CH_2$—$CH_2$—$NR^{12}$—;
—$NR^{12}$—$CH_2$—$CH_2$—$CH_2$—;
—$NR^{12}$—$CH_2$—$CH_2$—$NR^{12}$—;
—$CH_2$—$CH_2$—$CH_2$—$CH_2$—$CH_2$—;
—$CH_2$—$CH_2$—$NR^{12}$—$CH_2$—$CH_2$—;
—$CH_2$—$CH_2$—$CH_2$—$NR^{12}$—$CH_2$—;
—$CH_2$—$NR^{12}$—$CH_2$—$CH_2$—$CH_2$—;
—$CH_2$—$CH_2$—$CH_2$—$CH_2$—$NR^{12}$—; or
—$NR^{12}$—$CH_2$—$CH_2$—$CH_2$—$CH_2$—;

wherein $R^{12}$ represents hydrogen, a group of the formula —$CH_2CH_2OH$, —$CO$—$CH_3$, —$SO_2$—$CH_3$, or an alkyl group;

or $R^6$ and $R^7$ independently of each other represent hydrogen or methyl.

In one embodiment, $R^1$ represents hydrogen. In a second embodiment, $R^1$ represents alkyl, in particular methyl.

In a further embodiment, $R^2$ represents hydrogen, an alkyl group, an acyl group, or an isoxazolyl group, which isoxazolyl group may optionally be substituted with one or more substituents selected from the group consisting of alkyl or alkoxy.

In a still further embodiment, $R^2$ represents an oxo-tetrahydrofuryl group, or an isoxazolyl-alkyl group, which isoxazolyl group may optionally be substituted with one or more substituents selected from the group consisting of alkyl or alkoxy.

In a further embodiment, $R^2$ represents an alkyl group substituted with one or more hydroxy or carboxy. In a special embodiment, $R^2$ represents a $C_{3-6}$-alkyl substituted with hydroxy and carboxy, such as a hydroxybutyric acid group.

In a special embodiment, $R^2$ represents hydrogen. In a further embodiment, $R^2$ represents (3-methoxy-5-methyl-isoxazol-4-yl)-methyl. In a still further embodiment, $R^2$ represents alkyl, in particular methyl. In a further embodiment, $R^2$ represents 2-oxo-tetrahydrofur-3-yl. In a still further embodiment, $R^2$ represents 4-hydroxybutyric acid-2-yl.

In a further embodiment, $R^5$ represents a phenyl group, which group may optionally be substituted one or more times with halogen, $CF_3$, —$OCF_3$, $NO_2$, amino, aminosulfonyl, alkyl, alkoxy or phenyl. In a special embodiment, $R^5$ represents phenyl substituted in the 4-position with halogen, $CF_3$, $NO_2$, amino, alkyl, or alkoxy. In a further special embodiment, $R^5$ represents phenyl, 4-chlorophenyl, 4-trifluoromethylphenyl, 4-methylphenyl, 4-methoxyphenyl, 4-ethoxycarbonylphenyl, 4-bromophenyl, 4-trifluoromethoxyphenyl, or 4-(N,N-dimethylsulfamoyl)phenyl.

In a still further embodiment, $R^5$ represents a thienyl group, a pyridyl group, a pyrimidyl group, a pyridazinyl group, a pyrazinyl group, or a thiazolyl group, which groups may optionally be substituted one or more times with halogen, $CF_3$, $NO_2$, amino, alkyl, alkoxy or phenyl. In a special embodiment, $R^5$ represents 5-phenyl-thien-2-yl, 5-chloropyrid-2-yl, 6-chloropyrid-3-yl, 5-chloropyrimid-2-yl, 2-chloropyrimid-5-yl, 6-chloropyridazin-3-yl, 5-chloropyrazin-2-yl, 5-chlorothien-2-yl, 5-chloro-1,1-dioxy-thien-2-yl, 5-chlorothiazol-2-yl, 2-chlorothiazol-5-yl.

In a further embodiment, $R^5$ represents a phenyl group, a benzyl group, or a 5 or 6-membered monocyclic heterocyclic group, which groups may optionally be substituted one or more times with halogen, $CF_3$, $NO_2$, amino, alkyl, alkoxy or phenyl.

In one embodiment, $R^6$ and $R^7$ together form a fused 5 to 7 membered ring composed by one of the following bridging bivalent radicals (read in the direction $R^6$ to $R^7$): —$CH_2$—$CH_2$—$CH_2$—; —$NR^{12}$—$CH_2$—$CH_2$—; —$CH_2$—$CH_2$—$NR^{12}$—; —$CH_2$—$NR^{12}$—$CH_2$—; —$CH_2$—$CH_2$—$CH_2$—$CH_2$—; —$CH_2$—$CH_2$—$NR^{12}$—$CH_2$—; —$CH_2$—$NR^{12}$—$CH_2$—$CH_2$—; —$CH_2$—$CH_2$—$CH_2$—$NR^{12}$—; —$NR^{12}$—$CH_2$—$CH_2$—$CH_2$—; —$CH_2$—$CH_2$—$CH_2$—$CH_2$—$CH_2$—; —$CH_2$—$CH_2$—$NR^{12}$—$CH_2$—$CH_2$—; —$CH_2$—$CH_2$—$CH_2$—$NR^{12}$—$CH_2$—; —$CH_2$—$NR^{12}$—$CH_2$—$CH_2$—$CH_2$—; —$CH_2$—$CH_2$—$CH_2$—$CH_2$—$NR^{12}$—; or —$NR^{12}$—$CH_2$—$CH_2$—$CH_2$—$CH_2$—; wherein $R^{12}$ represents hydrogen, a group of the formula —$CH_2CH_2OH$, or an alkyl group.

In a further embodiment, $R^6$ and $R^7$ independently of each other represent hydrogen or methyl. In a special embodiment $R^6$ represents hydrogen and $R^7$ represents hydrogen. In a further special embodiment $R^6$ represents methyl and $R^7$ represents methyl.

In a still further embodiment, $R^6$ and $R^7$ together form a fused 5 to 7 membered ring composed by one of the following bridging bivalent radicals (read in the direction $R^6$ to $R^7$): —$CH_2$—$NR^{12}$—$CH_2$—; —$CH_2$—$CH_2$—$CH_2$—$CH_2$—; —$CH_2$—$CH_2$—$NR^{12}$—$CH_2$—; or —$CH_2$—$NR^{12}$—$CH_2$—$CH_2$—; wherein $R^{12}$ represents hydrogen, a group of the formula —$CH_2CH_2OH$, or an alkyl group.

In a further embodiment, $R^{12}$ represents hydrogen. In a still further embodiment, $R^{12}$ represents an alkyl group, such as methyl or ethyl. In a further embodiment, $R^{12}$ represents —CO—$CH_3$. In a still further embodiment, $R^{12}$ represents —$SO_2$—$CH_3$.

In a further embodiment, $R^{12}$ represents hydrogen, a group of the formula —$CH_2CH_2OH$, or an alkyl group.

In a preferred embodiment, the isatin derivatives of the invention may be characterised by the general formula (II)

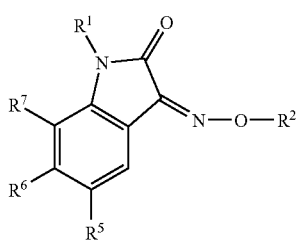
(II)

or a pharmaceutically acceptable salt thereof,
wherein,
$R^1$ represents hydrogen or an alkyl group;
$R^2$ represents hydrogen, an alkyl group, an acyl group, an oxo-tetrahydrofuryl group, an isoxazolyl-alkyl group, or an isoxazolyl group, which alkyl group may optionally be substituted with one or more hydroxy or carboxy, and which isoxazolyl group may optionally be substituted with one or more substituents selected from the group consisting of alkyl or alkoxy;

$R^5$ represents a phenyl group, a benzyl group, or a 5 or 6-membered monocyclic heterocyclic group, which groups may optionally be substituted one or more times with halogen, $CF_3$, —$OCF_3$, $NO_2$, amino, aminosulfonyl, alkyl, alkoxy, alkoxycarbonyl, or phenyl;

$R^6$ and $R^7$ together form a fused 5 to 7 membered ring composed by one of the following bridging bivalent radicals (read in the direction $R^6$ to $R^7$):
—$CH_2$—$CH_2$—;
—$CH_2$—$CH_2$—$CH_2$—;
—$NR^{12}$—$CH_2$—$CH_2$—;
—$CH_2$—$CH_2$—$NR^{12}$—;
—$CH_2$—$NR^{12}$—$CH_2$—;
—$NR^{12}$—$CH_2$—$NR^{12}$—;
—$CH_2$—$CH_2$—$CH_2$—$CH_2$—;
—$CH_2$—$CH_2$—$NR^{12}$—$CH_2$—;
—$CH_2$—$CH_2$—$NR^{12}$—$CH_2$—$CH_2$—;
—$CH_2$—$CH_2$—$CH_2$—$NR^{12}$—;
—$NR^{12}$—$CH_2$—$CH_2$—$CH_2$—;
—$NR^{12}$—$CH_2$—$CH_2$—$NR^{12}$—;
—$CH_2$—$CH_2$—$CH_2$—$CH_2$—$CH_2$—;
—$CH_2$—$CH_2$—$NR^{12}$—$CH_2$—$CH_2$—;
—$CH_2$—$CH_2$—$CH_2$—$NR^{12}$—$CH_2$—;
—$CH_2$—$NR^{12}$—$CH_2$—$CH_2$—$CH_2$—;
—$CH_2$—$CH_2$—$CH_2$—$NR^{12}$—; or
—$NR^{12}$—$CH_2$—$CH_2$—$CH_2$—$CH_2$—;
wherein $R^{12}$ represents hydrogen, a group of the formula —$CH_2CH_2OH$, —CO—$CH_3$, —$SO_2$—$CH_3$, or an alkyl group;
or $R^6$ and $R^7$ independently of each other represent hydrogen or methyl.

In another preferred embodiment, the isatin derivatives of the invention may be characterised by the general formula (III)

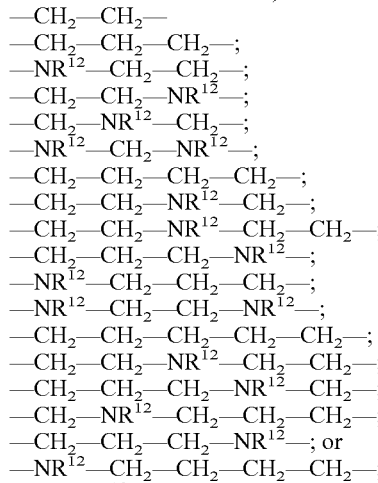
(III)

wherein
$R^1$ represents hydrogen or an alkyl group;
$R^2$ represents hydrogen, an alkyl group, an acyl group, an oxo-tetrahydrofuryl group, an isoxazolyl-alkyl group, or an isoxazolyl group, which alkyl group may optionally be substituted with one or more hydroxy or carboxy, and which isoxazolyl group may optionally be substituted with one or more substituents selected from the group consisting of alkyl or alkoxy;

$R^5$ represents a phenyl group, a benzyl group, or a 5 or 6-membered monocyclic heterocyclic group, which groups may optionally be substituted one or more times with halogen, $CF_3$, —$OCF_3$, $NO_2$, amino, aminosulfonyl, alkyl, alkoxy, alkoxycarbonyl, or phenyl; and $R^{12}$ represents hydrogen, a group of the formula —$CH_2CH_2OH$, —CO—$CH_3$, —$SO_2$—$CH_3$, or an alkyl group.

In a more preferred embodiment, the isatin derivatives of the general formula (II) is 7-ethyl-5-phenyl-1,6,7,8-tetrahydrobenzo[2,1-b: 3,4-c]dipyrrole-2,3-dione-3-methyloxime;

5-(4-chlorophenyl)-7-methyl-1,6,7,8-tetrahydrobenzo[2,1-b:3,4-c]dipyrrole-2,3-dione-3-oxime;

7-ethyl-5-phenyl-1,6,7,8-tetrahydrobenzo[2,1-b:3,4-c]dipyrrole-2,3-dione-3-oxime;

7-methyl-5-phenyl-1,6,7,8-tetrahydrobenzo[2,1-b:3,4-c]dipyrrole-2,3-dione-3-oxime;

7-ethyl-5-phenyl-1,6,7,8-tetrahydrobenzo[2,1-b:3,4-c]dipyrrole-2,3-dione-3-acetyloxime;

7-Ethyl-5-(4-chlorophenyl)-1,6,7,8-tetrahydrobenzo[2,1-b: 3,4-c]dipyrrole-2,3-dione-3-oxime hydrochloric acid salt;

7-Ethyl-5-(4-chlorophenyl)-1,6,7,8-tetrahydrobenzo[2,1-b: 3,4-c]dipyrrole-2,3-dione-3-methyloxime;

or a pharmaceutically acceptable salt thereof.

In a third preferred embodiment, the isatin derivatives of the invention may be characterised by the general formula (IV), (V) or (VI):

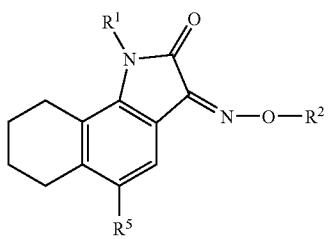

(IV)

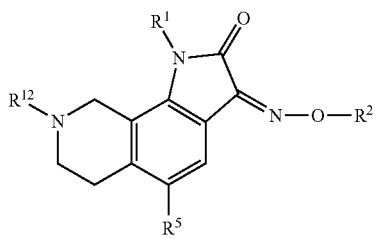

(V)

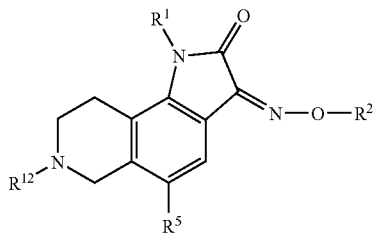

(VI)

wherein $R^1$ represents hydrogen or an alkyl group;

$R^2$ represents hydrogen, an alkyl group, an acyl group, an oxo-tetrahydrofuryl group, an isoxazolyl-alkyl group, or an isoxazolyl group, which alkyl group may optionally be substituted with one or more hydroxy or carboxy, and which isoxazolyl group may optionally be substituted with one or more substituents selected from the group consisting of alkyl or alkoxy;

$R^5$ represents a phenyl group, a benzyl group, or a 5 or 6-membered monocyclic heterocyclic group, which groups may optionally be substituted one or more times with halogen, $CF_3$, $-OCF_3$, $NO_2$, amino, aminosulfonyl, alkyl, alkoxy, alkoxycarbonyl, or phenyl; and $R^{12}$ represents hydrogen, a group of the formula $-CH_2CH_2OH$, $-CO-CH_3$, $-SO_2-CH_3$, or an alkyl group.

In a more preferred embodiment, the isatin derivatives of the general formula (IV) is 5-[5-phenyl-2-thienyl]-6,7,8,9-tetrahydro-1-H-pyrrolo[3.2-h]naphthalene-2,3-dione-3-oxime;

5-(4-Chlorophenyl)-6,7,8,9-tetrahydro-1-H-pyrrolo[3.2-h]naphthalene-2,3-dione-3-oxime;

5-(5-chloropyrid-2-yl)-6,7,8,9-tetrahydro-1-H-pyrrolo[3.2-h]naphthalene-2,3-dione-3-oxime;

5-(6-chloropyrid-3-yl)-6,7,8,9-tetrahydro-1-H-pyrrolo[3.2-h]naphthalene-2,3-dione-3-oxime;

5-(5-chloropyrimid-2-yl)-6,7,8,9-tetrahydro-1-H-pyrrolo[3.2-h]naphthalene-2,3-dione-3-oxime;

5-(2-chloropyrimid-5-yl)-6,7,8,9-tetrahydro-1-H-pyrrolo[3.2-h]naphthalene-2,3-dione-3-oxime;

5-(6-chloropyridazin-3-yl)-6,7,8,9-tetrahydro-1-H-pyrrolo[3.2-h]naphthalene-2,3-dione-3-oxime;

5-(5-chloropyrazin-2-yl)-6,7,8,9-tetrahydro-1-H-pyrrolo[3.2-h]naphthalene-2,3-dione-3-oxime;

5-(5-chlorothien-2-yl)-6,7,8,9-tetrahydro-1-H-pyrrolo[3.2-h]naphthalene-2,3-dione-3-oxime;

5-(5-chloro-1,1-dioxy-thien-2-yl)-6,7,8,9-tetrahydro-1-H-pyrrolo[3.2-h]naphthalene-2,3-dione-3-oxime;

5-(5-chlorothiazol-2-yl)-6,7,8,9-tetrahydro-1-H-pyrrolo[3.2-h]naphthalene-2,3-dione-3-oxime;

5-(2-chlorothiazol-5-yl)-6,7,8,9-tetrahydro-1-H-pyrrolo[3.2-h]naphthalene-2,3-dione-3-oxime;

5-(4-Chlorophenyl)-6,7,8,9-tetrahydro-1-H-pyrrolo[3.2-h]naphthalene-2,3-dione-3-O-(3-(2-oxo)tetrahydrofuryl)oxime;

5-(4-Chlorophenyl)-6,7,8,9-tetrahydro-1-H-pyrrolo[3.2-h]naphthalene-2,3-dione-3-O-(4-hydroxybutyric acid-2-yl)oxime;

5-(5-chloropyrid-2-yl)-6,7,8,9-tetrahydro-1-H-pyrrolo[3.2-h]naphthalene-2,3-dione-3-O-(4-hydroxybutyric acid-2-yl)oxime;

5-(6-chloropyrid-3-yl)-6,7,8,9-tetrahydro-1-H-pyrrolo[3.2-h]naphthalene-2,3-dione-3-O-(4-hydroxybutyric acid-2-yl)oxime;

5-(5-chloropyrimid-2-yl)-6,7,8,9-tetrahydro-1-H-pyrrolo[3.2-h]naphthalene-2,3-dione-3-O-(4-hydroxybutyric acid-2-yl)oxime;

5-(2-chloropyrimid-5-yl)-6,7,8,9-tetrahydro-1-H-pyrrolo[3.2-h]naphthalene-2,3-dione-3-O-(4-hydroxybutyric acid-2-yl)oxime;

5-(6-chloropyridazin-3-yl)-6,7,8,9-tetrahydro-1-H-pyrrolo[3.2-h]naphthalene-2,3-dione-3-O-(4-hydroxybutyric acid-2-yl)oxime;

5-(5-chloropyrazin-2-yl)-6,7,8,9-tetrahydro-1-H-pyrrolo[3.2-h]naphthalene-2,3-dione-3-O-(4-hydroxybutyric acid-2-yl)oxime;

5-(5-chlorothien-2-yl)-6,7,8,9-tetrahydro-1-H-pyrrolo[3.2-h]naphthalene-2,3-dione-3-O-(4-hydroxybutyric acid-2-yl)oxime;

5-(5-chloro-1,1-dioxy-thien-2-yl)-6,7,8,9-tetrahydro-1-H-pyrrolo[3.2-h]naphthalene-2,3-dione-3-O-(4-hydroxybutyric acid-2-yl)oxime;

5-(5-chlorothiazol-2-yl)-6,7,8,9-tetrahydro-1-H-pyrrolo[3.2-h]naphthalene-2,3-dione-3-O-(4-hydroxybutyric acid-2-yl)oxime;

5-(2-chlorothiazol-5-yl)-6,7,8,9-tetrahydro-1-H-pyrrolo[3.2-h]naphthalene-2,3-dione-3-O-(4-hydroxybutyric acid-2-yl)oxime;

or a pharmaceutically acceptable salt thereof.

In a more preferred embodiment, the isatin derivatives of the general formula (V) is 5-(4-Chlorophenyl)-8-methyl-6,7,8,9-tetrahydro-1-H-pyrrolo[3.2-h]isoquinoline-2,3-dione-3-oxime;
5-(4-Bromophenyl)-8-methyl-6,7,8,9-tetrahydro-1-H-pyrrolo[3.2-h]isoquinoline-2,3-dione-3-oxime;
5-(4-Trifluoromethoxyphenyl)-8-methyl-6,7,8,9-tetrahydro-1-H-pyrrolo[3.2-h]isoquinoline-2,3-dione-3-oxime;
5-(4-Trifluoromethylphenyl)-8-methyl-6,7,8,9-tetrahydro-1-H-pyrrolo[3.2-h]isoquinoline-2,3-dione-3-oxime;
5-(4-Toluyl)-8-methyl-6,7,8,9-tetrahydro-1-H-pyrrolo[3.2-h]isoquinoline-2,3-dione-3-oxime;
5-(4-Methoxyphenyl)-8-methyl-6,7,8,9-tetrahydro-1-H-pyrrolo[3.2-h]isoquinoline-2,3-dione-3-oxime;
8-Methyl-5-(4-(N,N-dimethylsulfamoyl)phenyl)-6,7,8,9-tetrahydro-1H-pyrrolo[3,2-h]isoquinoline-2,3-dione-3-O-((3-methoxy-5-methyl-isoxazol-4-yl)methyl)oxime;
8-Methyl-5-phenyl-6,7,8,9-tetrahydro-1H-pyrrolo[3,2-h]isoquinoline-2,3-dione-3-oxime;
8-Methyl-5-(4-nitrophenyl)-6,7,8,9-tetrahydro-1H-pyrrolo[3,2-h]isoquinoline-2,3-dione-3-oxime;
8-Methyl-5-(4-fluorophenyl)-6,7,8,9-tetrahydro-1H-pyrrolo[3,2-h]isoquinoline-2,3-dione-3-oxime;
8-Methyl-5-phenyl-6,7,8,9-tetrahydro-1H-pyrrolo[3,2-h]isoquinoline-2,3-dione-3-acetyloxime;
8-Methyl-5-(4-ethylbenzoyl)-6,7,8,9-tetrahydro-1H-pyrrolo[3,2-h]isoquinoline-2,3-dione-3-oxime;
8-Acetyl-5-(4-chlorophenyl)-6,7,8,9-tetrahydro-1-H-pyrrolo[3.2-h]isoquinoline-2,3-dione-3-oxime;
5-(4-Chlorophenyl)-8-methylsulphonyl-6,7,8,9-tetrahydro-1-H-pyrrolo[3.2-h]isoquinoline-2,3-dione-3-oxime;
or a pharmaceutically acceptable salt thereof.

In a more preferred embodiment, the isatin derivatives of the general formula (VI) is 7-Methyl-5-(4-chlorophenyl)-6,7,8,9-tetrahydro-1H-pyrrolo[3,2-f]isoquinoline-2,3-dione-3-oxime;
5-Phenyl-7-methyl-6,7,8,9-tetrahydro-1-methyl-pyrrolo[3.2-f]isoquinoline-2,3-dione-3-oxime;
7-Methyl-5-phenyl-6,7,8,9-tetrahydro-1H-pyrrolo[3,2-f]isoquinoline-2,3-dione-3-oxime;
7-ethyl-5-phenyl-6,7,8,9-tetrahydro-1H-pyrrolo[3,2-f]isoquinoline-2,3-dione-3-oxime;
or a pharmaceutically acceptable salt thereof.

In a fourth preferred embodiment, the isatin derivatives of the invention may be characterised by the general formula (VII)

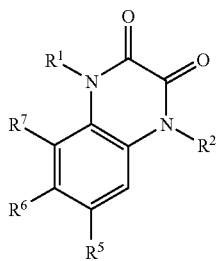

(VII)

or a pharmaceutically acceptable salt thereof,
wherein,
$R^1$ represents hydrogen or an alkyl group;
$R^2$ represents hydrogen, an alkyl group, an acyl group, an oxo-tetrahydrofuryl group, an isoxazolyl-alkyl group, or an isoxazolyl group, which alkyl group may optionally be substituted with one or more hydroxy or carboxy, and which isoxazolyl group may optionally be substituted with one or more substituents selected from the group consisting of alkyl or alkoxy;
$R^5$ represents a phenyl group, a benzyl group, or a 5 or 6-membered monocyclic heterocyclic group, which groups may optionally be substituted one or more times with halogen, $CF_3$, $-OCF_3$, $NO_2$, amino, aminosulfonyl, alkyl, alkoxy, alkoxycarbonyl, or phenyl;
$R^6$ and $R^7$ together form a fused 5 to 7 membered ring composed by one of the following bridging bivalent radicals (read in the direction $R^6$ to $R^7$):

—$CH_2$—$CH_2$
—$CH_2$—$CH_2$—$CH_2$—;
—$NR^{12}$—$CH_2$—$CH_2$—;
—$CH_2$—$CH_2$—$NR^{12}$—;
—$CH_2$—$NR^{12}$—$CH_2$—;
—$NR^{12}$—$CH_2$—$NR^{12}$—;
—$CH_2$—$CH_2$—$CH_2$—$CH_2$—;
—$CH_2$—$CH_2$—$NR^{12}$—$CH_2$—;
—$CH_2$—$NR^{12}$—$CH_2$—$CH_2$—;
—$CH_2$—$CH_2$—$CH_2$—$NR^{12}$—;
—$NR^{12}$—$CH_2$—$CH_2$—$CH_2$—;
—$NR^{12}$—$CH_2$—$CH_2$—$NR^{12}$—;
—$CH_2$—$CH_2$—$CH_2$—$CH_2$—$CH_2$—;
—$CH_2$—$CH_2$—$NR^{12}$—$CH_2$—$CH_2$—;
—$CH_2$—$CH_2$ $CH_2$—$NR^{12}$—$CH_2$—;
—$CH_2$—$NR^{12}$—$CH_2$—$CH_2$—$CH_2$—;
—$CH_2$—$CH_2$—$CH_2$—$CH_2$—$NR^{12}$—; or
—$NR^{12}$—$CH_2$—$CH_2$—$CH_2$—$CH_2$—;

wherein $R^{12}$ represents hydrogen, a group of the formula —$CH_2CH_2OH$, —$CO$—$CH_3$, —$SO_2$—$CH_3$, or an alkyl group;
or $R^6$ and $R^7$ independently of each other represent hydrogen or methyl.

In a fifth preferred embodiment, the isatin derivatives of the invention may be characterised by the general formula (VIII)

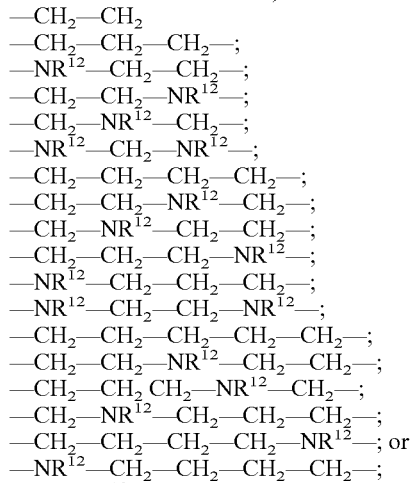

(VIII)

wherein
$R^1$ represents hydrogen or an alkyl group;
$R^2$ represents hydrogen, an alkyl group, an acyl group, an oxo-tetrahydrofuryl group, an isoxazolyl-alkyl group, or an isoxazolyl group, which alkyl group may optionally be substituted with one or more hydroxy or carboxy, and which isoxazolyl group may optionally be substituted with one or more substituents selected from the group consisting of alkyl or alkoxy;
$R^5$ represents a phenyl group, a benzyl group, or a 5 or 6-membered monocyclic heterocyclic group, which groups may optionally be substituted one or more times with halogen, $CF_3$, $-OCF_3$, $NO_2$, amino, aminosulfonyl, alkyl, alkoxy, alkoxycarbonyl, or phenyl; and
$R^{12}$ represents hydrogen, a group of the formula —$CH_2CH_2OH$, —$CO$—$CH_3$, —$SO_2$—$CH_3$, or an alkyl group.

In a more preferred embodiment, the isatin derivatives of the general formula (VII) is 5-(4-Chlorophenyl)-1,4,7,8,9,10-hexahydropyrido-8-methyl[4,3-f]quinoxaline-2,3-dione;

5-(4-nitrophenyl)-1,4,7,8,9,10-hexahydropyrido-8-ethyl [4,3-f]quinoxaline-2,3-dione;

or a pharmaceutically acceptable salt thereof.

Definition of Substituents

In the context of this invention halogen represents a fluorine, a chlorine, a bromine or an iodine atom.

In the context of this invention an alkyl group designates a univalent saturated, straight or branched hydrocarbon chain. The hydrocarbon chain preferably contain of from one to eighteen carbon atoms ($C_{1-8}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention an alkoxy group designates an "alkyl-O-" group, wherein alkyl is as defined above.

In the context of this invention an acyl group designates a carboxy group (—COOH) or an alkylcarbonyl group (alkyl-CO—), wherein alkyl is as defined above. Examples of preferred acyl groups of the invention include carboxy, acetyl, and propionyl.

In the context of this invention an amino group may be a primary (—NH$_2$), secondary (—NH-alkyl), or tertiary (—N(alkyl)$_2$) amino group, i.e. it may be substituted once or twice with an alkyl group as defined above.

In the context of this invention a heterocyclic group is a compound, which holds one or more heteroatoms in its ring structure. Preferred heteroatoms include nitrogen (N), oxygen (O), and sulphur (S). The heterocyclic group may in particular be aromatic (i.e. a heteroaryl), saturated or partially saturated. Preferred heterocyclic monocyclic groups of the invention include 5- and 6 membered heterocyclic monocyclic groups.

Examples of preferred aromatic 5- or 6-membered heterocyclic groups of the invention include 1,3,2,4- or 1,3,4,5-dioxadiazolyl, dioxatriazinyl, dioxazinyl, 1,2,3-, 1,2,4-, 1,3, 2- or 1,3,4-dioxazolyl, 1,3,2,4- or 1,3,4,5-dithiadiazolyl, dithiatriazinyl, dithiazinyl, 1,2,3-dithiazolyl, 2- or 3-furanyl, furazanyl, 1, 2 or 4-imidazolyl, isoindazolyl, isothiazol-3,4 or 5-yl, isoxazol-3,4 or 5-yl, 1,2,3-, 1,2,4-, 1,2,5- or 1,3,4-oxadiazol-3,4 or 5-yl, oxatetrazinyl, oxatriazinyl, 1,2,3,4- or 1,2, 3,5-oxatriazolyl, oxazol-2,4 or 5-yl, 2 or 3-pyrazinyl, 1,3 or 4-pyrazolyl, 3 or 4-pyridazinyl, 2,3 or 4-pyridinyl, 2,4 or 5-pyrimidinyl, 1,2 or 3-pyrrolyl(azolyl), 1,2,3,4- or 2,1,3,4-tetrazolyl, thiadiazol-3,4 or 5-yl, thiazol-2,4 or 5-yl, 2 or 3-thienyl, 1,2,3-, 1,2,4- or 1,3,5-triazinyl, and 1,2,3-, 1,2,4-, 2,1,3- or 4,1,2-triazolyl. Most preferred aromatic heterocyclic groups of the invention furan-2-yl, furan-3-yl, 2-, 4- or 5-imidazolyl, 3-, 4- or 5-isoxazolyl, 1-, 2- or 3-pyridinyl, and 1- or 2-thienyl.

Examples of preferred saturated or partially saturated 5- or 6-membered heterocyclic groups of the invention include 1,3,5,6,2-dioxadiazinyl, 1,2,3,4,5-, 1,2,3,5,4-dioxadiazolyl, dioxanyl, 1,3-dioxolyl, 1,3,5,6,2-dithiadiazinyl, 1,2,3,4,5- or 1,2,3,5,4-dithiadiazolyl, 2-isoimidazolyl, isopyrrolyl, isotetrazolyl, 1,2,3- or 1,2,4-isotriazolyl, morpholinyl, oxadiazinyl, 1,2,4-, 1,2,6-, 1,3,2-, 1,3,6- or 1,4,2-oxazinyl, piperazinyl, homopiperazinyl, piperidinyl, 1,2-, 1,3- or 1,4-pyranyl, and 1,2,3-pyrrolidinyl.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or I-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "Enantiomers, Racemates and Resolutions", John Wiley and Sons, New York (1981). Optical active compounds can also be prepared from optical active starting materials.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The chemical compound of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Labelled Compounds

The compounds of the invention may be used in their labelled or unlabelled form. In the context of this invention "label" stands for the binding of a marker to the compound of interest that will allow easy quantitative detection of said compound.

The labeled compounds of the invention may be useful as diagnostic tools, radio tracers, or monitoring agents in various diagnostic methods, and for in vivo receptor imaging.

In the labelled compound one or more atoms has been changed into an isotope of the naturally occurring atom. Labelled compounds includes though not limited to $^2$H (deuterium), $^3$H (tritium), $^{13}$C, $^{14}$C, $^{131}$I, $^{125}$I, $^{123}$I, and $^{18}$F.

In a preferred embodiment the physical detection method is selected from PET, SPECT; MRS, MRI, CAT, or combinations thereof.

Methods of Preparation

The isatin derivatives of the invention may be prepared by conventional methods for chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.01 to about 500 mg of active ingredient per individual dose, preferably of from about 0.1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.01 µg/kg i.v. and 0.1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Biological Activity

As demonstrated in the working examples, the compounds of the invention show neutrophic activity. The neurotrophic activity has not been ascribed to a specific step in the interaction between NGF and its receptor or in the NGF signal transduction pathway.

The neurotrophic activity of the compounds of the invention makes them useful for the treatment or prevention of various degenerative diseases of the nervous system.

Moreover, the compounds of the invention are considered particularly useful for the treatment of neuropathy and in particular peripheral neuropathy caused by e.g. genetic abnormalities and other conditions such as diabetes, polio, herpes and AIDS, and most especially neuropathy and peripheral neuropathy experienced by most cancer patients after or during chemotherapy.

The compounds of the present invention are considered particularly useful for the treatment of traumatic lesions of peripheral nerves, the medulla, and/or the spinal cord, and in the treatment of cerebral ischaemia, e.g. ischaemic neuronal damage following cardiac arrest, stroke, or postasphyxial brain damage in new-borns, or following near-drowning.

Finally the compounds of the present invention are considered particularly useful for increasing the survival of neuronal grafts.

Methods of Therapy

In another aspect the invention provides a method for the treatment or alleviation of diseases or disorders or conditions of living animal bodies, including humans, which diseases, disorders or conditions are responsive to responsive to the activity of a neurotrophic agent, and which method comprises administering to such a living animal body, including a human, in need thereof an effective amount of a chemical compound of the invention.

In a preferred embodiment the disease or disorder or condition is responsive to the activation or potentiation of nerve growth factor(s).

In another preferred embodiment the invention provides a method for the treatment of a traumatic lesion of peripheral nerves, the medulla, the spinal cord, cerebral ischaemic neuronal damage, neuropathy, including peripheral neuropathy.

In a third preferred embodiment the disease is a neurodegenerative disease.

In a more preferred embodiment the neurodegenerative disease is dementia, Alzheimer's disease, Parkinson's disease, Huntington's disease, amyotrophic lateral sclerosis, or neurodegenerative diseases of the eye, including photoreceptor loss in the retina in patients afflicted with macular degeneration, retinitis pigmentosa, glaucoma, and similar diseases.

In a fourth preferred embodiment the invention provides a method for preventing the degenerative changes connected with a neurodegenerative disease.

In a more preferred embodiment the neurodegenerative disease is cerebral ischaemic neuronal damage, neuropathy and especially peripheral neuropathy, Alzheimer's disease, Huntington's disease, Parkinson's disease, or amyotrophic lateral sclerosis.

Specific diseases contemplated according to the invention include the excitatory amino acid dependent, and in particular glutamate and/or aspartate dependent diseases, disorders and conditions like psychosis, anoxia, ischaemia, Parkinsonism, convulsions, migraine, and amyotrophic lateral sclerosis (ALS).

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

BRIEF DESCRIPTION OF THE DRAWINGS

The present invention is further illustrated by reference to the accompanying drawing, in which.

EXAMPLES

Figure 1:
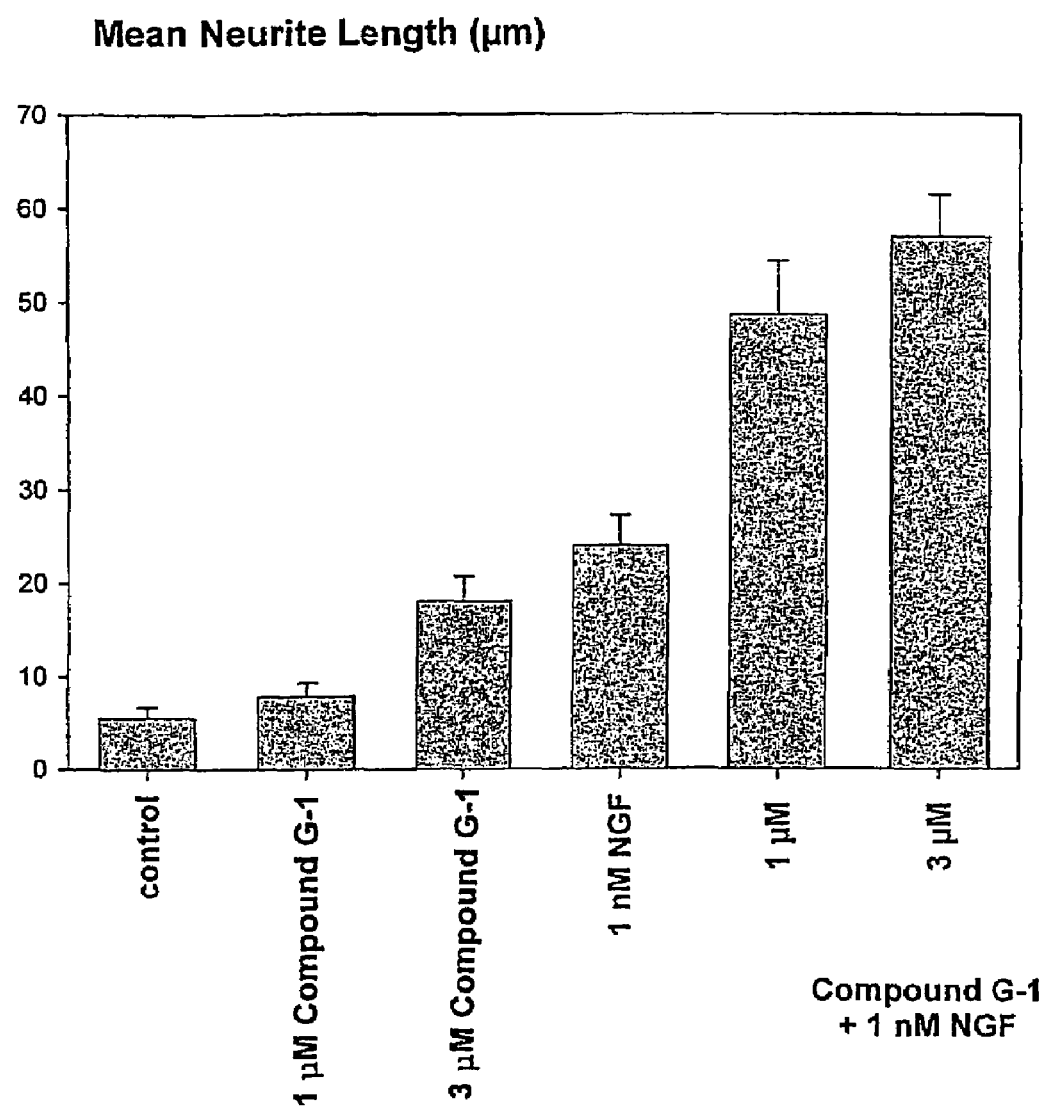
FIG. 1 illustrates the effect on the average neurite length±SEM (total neurite length/total cell number per well) of PC12 cells after two days of incubation with or without Compound G-1 and NGF.

The invention is further illustrated with reference to the following examples which are not intended to be in any way limiting to the scope of the invention as claimed.

Example 1

Preparatory Examples

General: All reactions involving air sensitive reagents or intermediates were performed under nitrogen and in anhydrous solvents. Magnesium sulphate was used as drying agent in the workup-procedures and solvents were evaporated under reduced pressure.

Method A

5-Bromo-8-nitroisoquinoline

A solution of potassium nitrate (120 g, 1.2 mol) in conc. sulphuric acid (500 ml) was added to a mixture of 5-bromoisoquinoline (219.4 g, 1.05 mol) and conc. sulphuric acid (400 ml) at below 10° C. during 1.5 h. The reaction was poured out on ice (4 l) and was neutralised by addition of conc. ammonium hydroxide (2 l) and ice (4 l). The crystals were filtered and air dried. Yield 216.9 g (82%). Mp 129-130° C.

Method B

5-Bromo-N-methyl-8-nitro-1,2,3,4-tetrahydroisoquinoline

5-Bromo-8-nitroisoquinoline (216.9 g, 0.86 mol) was added in portions during 10 min to a solution of dimethylsulphate (750 ml). Some heat was developed. The mixture was heated at 100° C. for 10 minutes. 5-Bromo-2-methyl-8-nitroquinolinium methyl sulphate precipitated. The mixture was cooled on ice and diethyl ether (1 l) was added. The crude mixture was filtered and crystals were isolated. The salt was solved in acetic acid (1.5 l). To the ice-cooled mixture was added: sodium borohydride (47 g, 1.24 mol) over 4 hours. The temperature was kept below 30° C. The crude mixture was evaporated and sodium hydroxide (2 l, 1 M) was added. The crystals were filtered. Yield 205.2 g (88%). Mp 85-87° C.

Method C 5-(4-Chlorophenyl)-N-methyl-8-nitro-1,2,3,4-tetrahydroisoquinoline

A mixture of 5-bromo-N-methyl-8-nitro-1,2,3,4-tetrahydroisoquinoline (4.07 g, 15 mmol), 4-chlorophenylboronic acid (3.5 g, 22.5 mmol), sodium carbonate (8.0 g, 75.5 mmol), 1,2-dimethoxyethane (60 ml), water (30 ml) and tetrakis(triphenyl-phosphine)palladium(0) (0.20 g, 0.17 mmol) was stirred at reflux for 3.5 h. Water (50 ml) was added and the mixture was extracted with ethyl acetate (100 ml). The crude mixture was recrystallized from ethanol (96%). Yield 3.62 g (80%). Mp 162-163° C.

8-Acetylamino-5-(4-chlorophenyl)-tetrahydro-1,2,3,4-naphthalene

Was prepared according to method C from 1-Acetylamino-4-bromo-5,6,7,8-tetrahydronaphthalene. Yield 62%. Mp 217-220° C.

4-(4-Chlorophenyl)-nitrobenzene

Was prepared according to method C from 4-bromonitrobenzene and 4-Chlorophenyl boronic acid. Yield 86%. Mp 141.6-145.2° C.

Method D

8-Amino-5-(4-chlorophenyl)-N-methyl-1,2,3,4-tetrahydroisoquinoline hydrochloric acid salt A mixture of 5-(4-Chlorophenyl)-N-methyl-8-nitro-1,2,3,4-tetrahydroiso-quinoline (3.47 g, 11.5 mmol), sulphuric acid (1 ml, 12 mmol), Raney nickel (1 ml, 50% slurry in water) and methanol (150 ml) was stirred under hydrogen for 1.5 h. The crude mixture was filtered through celite and was evaporated. Yield 3.2 g (90%). Mp 213-215° C.

4-Chlorophenyl)aniline

Was prepared according to method D from 4-(4-chlorophenyl)-nitrobenzene. The product was isolated as an oil. Yield 72%.

Method F 5-(4-Chlorophenyl)-8-methyl-6,7,8,9-tetrahydro-1-H-pyrrolo[3.2-h]isoquinoline-2,3-dione A mixture of 8-Amino-5-(4-chlorophenyl)-N-methyl-1,2,3,4-tetrahydroiso-quinoline hydrochloric acid salt (3.1 g, 10 mmol), chloral (1.5 ml, 15 mmol), sodium sulphate (14 g, 98.6 mmol), hydroxylamine hydrochloride (2.4 g, 15 mmol) and water (70 ml) was heated at reflux for 0.5 h. The mixture was allowed to reach room-temperature. The crystals were filtered and washed with water, followed by recrystallisation from ethanol (96%). The crystalline intermediate (2.0 g) was combined with methanesulphonic acid (20 ml) and heated for 15 min at 100° C. The crude mixture was poured out on ice and sodium hydroxide (25 ml, 10 M) was added. The crystalline product was recrystallized from ethanol (96%). Yield 0.54 g (29%). Mp decomp. 225° C.

5-(4-Chlorophenyl)-6,7,8,9-tetrahydro-1-H-pyrrolo[3.2-h]naphthalene-2,3-dione

Was prepared according to method F from 8-amino-5-(4-chlorophenyl)-N-methyl-1,2,3,4-naphthalene. Yield 52%. Mp 286.9-290.1° C.

5-(4-Chlorophenyl)isatin

Was prepared according to method F from 4-chlorophenyl)aniline. Yield 26%. Mp 246.3-251.5° C.

Method G 5-(4-Chlorophenyl)-8-methyl-6,7,8,9-tetrahydro-1-H-pyrrolo[3.2-h]isoquinoline-2,3-dione-3-oxime hydrochloric acid salt (Compound G-1)

A mixture of 5-(4-chlorophenyl)-8-methyl-6,7,8,9-tetrahydro-1-H-pyrrolo[3.2-h]isoquinoline-2,3-dione (0.50 g, 1.53 mmol), hydroxylamine hydrochloride (0.5 g, 7.2 mmol) and ethanol (5 ml, 96%) was stirred at room-temperature for 15 minutes. The colour shifted from yellow to red and the product precipitated. The product was filtered and 0.44 g (76%) was isolated. Mp decomp. 300-305° C.

5-(4-Chlorophenyl)-6,7,8,9-tetrahydro-1-H-pyrrolo[3.2-h]naphthalene-2,3-dione-3-oxime hydrochloric acid salt (Compound G-2)

Was prepared according to method G from 5-(4-chlorophenyl)-6,7,8,9-tetrahydro-1-H-pyrrolo[3.2-h]naphthalene-2,3-dione Yield 79%, Mp decomp. 250° C.

5-(4-Chlorophenyl)isatin-3-oxime (Compound G-3)

Was prepared according to method G from 5-(4-chlorophenyl)isatin. Yield 41%, Mp 236-237° C.

5-(4-Trifluoromethylphenyl)-8-methyl-6,7,8,9-tetrahydro-1-H-pyrrolo[3.2-h]isoquinoline-2,3-dione-3-oxime hydrochloric acid salt (Compound G-4)

Was prepared according to method G. Mp 295-300° C. decomp.

5-[5-phenyl-2-thienyl]-8-methyl-6,7,8,9-tetrahydro-1-H-pyrrolo[3.2-h]naphthalene-2,3-dione-3-oxime hydrochloric acid salt (Compound G-5)

Was prepared according to method G. Mp 267-268° C.

5-(4-Toluyl)-8-methyl-6,7,8,9-tetrahydro-1-H-pyrrolo[3.2-h]isoquinoline-2,3-dione-3-oxime methanesulphonic acid salt (Compound G-6)

Was prepared according to method G. Mp 225-230° C. decomp.

5-(4-Methoxyphenyl)-8-methyl-6,7,8,9-tetrahydro-1-H-pyrrolo[3.2-h]isoquinoline-2,3-dione-3-oxime methanesulphonic acid salt (Compound G-7)

Was prepared according to method G. Mp 228° C.

5-(4-Bromophenyl)-8-methyl-6,7,8,9-tetrahydro-1-H-pyrrolo[3.2-h]isoquinoline-2,3-dione-3-oxime hydrochloric acid salt (Compound G-8)

Was prepared according to method G. Mp>300° C. decomp.

5-(4-Trifluoromethoxyphenyl)-8-methyl-6,7,8,9-tetrahydro-1-H-pyrrolo[3.2-h]isoquinoline-2,3-dione-3-oxime hydrochloric acid salt (Compound G-9)

Was prepared according to method G. Mp>250° C. decomp.

5-(4-Chlorophenyl)-7-methyl-1,6,7,8-tetrahydrobenzo[2,1-b:3,4-c]dipyrrole-2,3-dione-3-oxime hydrochloric acid salt (Compound G-10)

Was prepared according to method G. Mp>250° C. decomp.

5-Phenyl-7-methyl-6,7,8,9-tetrahydro-1-methyl-pyrrolo[3.2-f]isoquinoline-2,3-dione-3-oxime hydrochloric acid salt (Compound G-11)

Was prepared according to method G. Mp 292-294° C.

8-Acetyl-5-(4-chlorophenyl)-6,7,8,9-tetrahydro-1-H-pyrrolo[3.2-h]isoquinoline-2,3-dione-3-oxime (Compound G-12)

Was prepared according to method G. Mp 250° C. decomp.

7-Ethyl-5-(4-chlorophenyl)-1,6,7,8-tetrahydrobenzo[2,1-b:3,4-c]dipyrrole-2,3-dione-3-oxime hydrochloric acid salt (Compound G-13)

Was prepared according to method G. Mp 220° C. decomp.

5-(4-Chlorophenyl)-8-methylsulphonyl-6,7,8,9-tetrahydro-1-H-pyrrolo[3.2-h]isoquinoline-2,3-dione-3-oxime (Compound G-14)

Was prepared according to method G. Mp 205° C. decomp.

5-(4-Chlorophenyl)-4,5-dimethylisatin-3-oxime (Compound G-15)

Was prepared from 5-(4-chlorophenyl)-4,5-dimethylisatin according to method G. Mp 250° C. decomp.

7-Methyl-5-(4-chlorophenyl)-6,7,8,9-tetrahydro-1H-pyrrolo[3,2-f]isoquinoline-2,3-dione-3-oxime hydrochloric acid salt (Compound G-16)

Was prepared according to method G. Mp 250° C. decomp.

7-Methyl-5-phenyl-6,7,8,9-tetrahydro-1H-pyrrolo[3,2-f]isoquinoline-2,3-dione-3-oxime hydrochloric acid salt (Compound G-17);

Was prepared according to method G. Mp 310° C.

5-(4-nitrophenyl)-1,4,7,8,9,10-hexahydropyrido-8-ethyl[4,3-f]quinoxaline-2,3-dione hydrochloric acid salt (Compound G-18);

Was prepared according to method G. Mp 300° C.

The following compounds can be prepared according to method G:
5-(5-chloropyrid-2-yl)-6,7,8,9-tetrahydro-1-H-pyrrolo[3.2-h]naphthalene-2,3-dione-3-oxime (Compound G-19)
5-(6-chloropyrid-3-yl)-6,7,8,9-tetrahydro-1-H-pyrrolo[3.2-h]naphthalene-2,3-dione-3-oxime (Compound G-20)
5-(5-chloropyrimid-2-yl)-6,7,8,9-tetrahydro-1-H-pyrrolo[3.2-h]naphthalene-2,3-dione-3-oxime (Compound G-21)
5-(2-chloropyrimid-5-yl)-6,7,8,9-tetrahydro-1-H-pyrrolo[3.2-h]naphthalene-2,3-dione-3-oxime (Compound G-22)
5-(6-chloropyridazin-3-yl)-6,7,8,9-tetrahydro-1-H-pyrrolo[3.2-h]naphthalene-2,3-dione-3-oxime (Compound G-23)
5-(5-chloropyrazin-2-yl)-6,7,8,9-tetrahydro-1-H-pyrrolo[3.2-h]naphthalene-2,3-dione-3-oxime (Compound G-24)
5-(5-chlorothien-2-yl)-6,7,8,9-tetrahydro-1-H-pyrrolo[3.2-h]naphthalene-2,3-dione-3-oxime (Compound G-25)
5-(5-chloro-1,1-dioxy-thien-2-yl)-6,7,8,9-tetrahydro-1-H-pyrrolo[3.2-h]naphthalene-2,3-dione-3-oxime (Compound G-26)
5-(5-chlorothiazol-2-yl)-6,7,8,9-tetrahydro-1-H-pyrrolo[3.2-h]naphthalene-2,3-dione-3-oxime (Compound G-27)
5-(2-chlorothiazol-5-yl)-6,7,8,9-tetrahydro-1-H-pyrrolo[3.2-h]naphthalene-2,3-dione-3-oxime (Compound G-28)

Method H

1-Amino-4-(4-chlorophenyl)-tetrahydro-5,6,7,8-naphthalene

A mixture of 1-Acetylamino-4-(4-chlorophenyl)-tetrahydro-5,6,7,8-naphthalene (1.65 g, 5.5 mmol), aqueous sodium hydroxide (20 ml, 4 M) and ethanol (96%) was stirred at reflux for 3 days. Water (50 ml) was added and the mixture was extracted with ethyl acetate (50 ml). The product was isolated as an oil. Yield 1.31 g (93%).

Method I

1-Acetylamino-4-bromo-5,6,7,8-tetrahydronaphthalene

To a mixture of 1-acetylamino-5,6,7,8-tetrahydronaphthalene (1.9 g, 10 mmol) in trifluoroacetic acid (20 ml) was added: bromine (0.55 ml, 10 mmol) solved in acetic acid (5 ml). The mixture was stirred for 15 min at room-temperature. Water (50 ml) was added and the crystals were filtered. Yield 2.6 g (97%). Mp=185.2-188.6° C.

Method J

1-Acetylamino-5,6,7,8-tetrahydronaphthalene

Acetic acid anhydride (20 ml) was added to a mixture of 1-amino-5,6,7,8-tetrahydronaphthalene (10 g, 68 mmol), sodium acetate (20 g, 245 mmol) and water (100 ml) at 5° C. The mixture was stirred at room-temperature for 15 minutes. The mixture was cooled on ice for 1 hour followed by filtration. The crystals were washed with water. Yield 13.0 g (100%).

Method K 5-(4-Chlorophenyl)-1,4,7,8,9,10-hexahydropyrido-8-methyl[4,3-f]quinoxaline-2,3-dione hydrochloric acid salt (Compound K-1)

A mixture of 4-chlorophenyl)-7,8-diamino-1-methyl-1,2,3,4-tetrahydroiso-quinoline (1.44 g, 5.0 mmol), oxalic acid dihydrate (2.0 g, 15.8 mmol) and hydrochloric acid (30 ml, 4 M) was stirred at reflux for 2 h. The crystalline precipitate was filtered. Yield 1.27 g, 67%. Mp>250° C.

Method L

8-Methyl-5-(4-(N,N-dimethylsulfamoyl)phenyl)-6,7,8,9-tetrahydro-1H-pyrrolo[3,2-h]isoquinoline-2,3-dione-3-O-((3-methoxy-5-methyl-isoxazol-4-yl)methyl)oxime methane sulphonic acid salt (Compound L-1)

A mixture of 8-methyl-5-(4-(N,N-dimethylsulfamoyl) phenyl)-6,7,8,9-tetrahydro-1H-pyrrolo[3,2-h]isoquinoline-2,3-dione (0.79 g, 2.0 mmol), 4-(amino-oxy-methyl)-3-methoxy-5-methylisoxazole (0.63 g, 2.67 mmol) and methanol (40 ml) was stirred at reflux for 2 h. Aqueous ammonia was added and the mixture was extracted dichloromethane.

The mixture was purified by column chromatography on silica gel, using a mixture of dichloromethane:methanol and concentrated ammonia (89:10:1) as eluent. The crude base was combined with methane sulphonic acid in isopropanol (5 ml, 0.1 M). The product was isolated as yellow crystals by filtration. Yield 0.25 g (20%). Mp 104° C.

Method M

7-Ethyl-5-(phenyl)-1,6,7,8-tetrahydrobenzo[2,1-b:3,4-c]dipyrrole-2,3-dione-3-methyloxime hydrochloric acid salt (Compound M-1)

A mixture of 7-ethyl-5-phenyl-1,6,7,8-tetrahydrobenzo[2,1-b:3,4-c]dipyrrole-2,3-dione (110 mg, 0.38 mmol), methoxylamine hydrochloride (90 mg, 1.1 mmol) and ethanol (10 ml, 99%) was stirred for 15 min at room-temperature. The mixture was evaporated to 5 ml. The precipitated product was isolated by filtration. Yield 50 mg, 37%. Mp>300° C.

7-Ethyl-5-(4-chlorophenyl)-1,6,7,8-tetrahydrobenzo[2,1-b: 3,4-c]dipyrrole-2,3-dione-3-methyloxime hydrochloric acid salt (Compound M-2)

Was prepared according to method M. Mp 245° C. decomp.

Method N

α-Phthalimidooxy-γ-butyrolactone, hydrochloride

To a solution of α-Bromo-γ-butyrolactone (3.0 mL, 36 mmol) in dimethylformamide (50 mL) was added N-hydroxyphthalimide (4.6 g, 28 mmol) followed by triethylamine (7.7 mL, 56 mmol). After stirring for 4 hours at room temperature the reaction was filtered and evaporated to dryness using an oil pump. Hydrochloric acid (1M, 28 mL) and water (20 mL) was added. The precipitate was filtered off and washed with water. Drying in the air gave 7.1 g of beige crystals.

α-Aminooxy-γ-butyrolactone hydrochloride

α-Phthalimidooxy-γ-butyrolactone (1.0 g, 4 mmol) was added to hydrochloric acid (1 M, 10 mL) at reflux. After 5 min. at reflux for 5 min and the reaction was cooled down on an ice bath and filtered. The filtrate was evaporated to dryness. Toluene was added and residual water removed azeotropic distillation. 0.75 g of the desired material was obtained.

5-(4-Chlorophenyl)-6,7,8,9-tetrahydro-1-H-pyrrolo [3.2-h]naphthalene-2,3-dione-3-O-(3-(2-oxo)tetrahydrofuryl)oxime (Compound N-1)

To a solution of 5-(4-Chlorophenyl)-6,7,8,9-tetrahydro-1-H-pyrrolo[3.2-h]naphthalene-2,3-dione (1.06 g, 2.7 mmol) in methanol (30 mL) heated to reflux, was added α-aminooxy-γ-butyrolactone (0.75 g, 4 mmol) dissolved in warm methanol (10 mL). Yellow crystals precipitate out. The reaction was heated at reflux for another 15 min and cooled to room temperature. The product was filtered off and washed with cold methanol 5-(4-Chlorophenyl)-6,7,8,9-tetrahydro-1-H-pyrrolo[3.2-h]naphthalene-2,3-dione-3-O-(3-(2-oxo)tetrahydrofuryl)oxime (1.2 g), was obtained. Mp 280-282° C.

Method O 5-(4-Chlorophenyl)-6,7,8,9-tetrahydro-1-H-pyrrolo [3.2-h]naphthalene-2,3-dione-3-O-(4-hydroxybutyric acid-2-yl)oxime (Compound O-1)

5-(4-Chlorophenyl)-6,7,8,9-tetrahydro-1-H-pyrrolo[3.2-h]naphthalene-2,3-dione-3-O-(3-(2-oxo)tetrahydrofuryl) oxime (0.75 g) was stirred at 80° C. for 30 min in water (25 ml) ethanol (5 ml, 96%) and 1 N NaOH (aq) in such amounts that assured a pH around 12. The reaction mixture was acidified with hydrochloric acid and the product precipitated. Mp 154.5° C.

The following compounds can be prepared according to method O:
5-(5-chloropyrid-2-yl)-6,7,8,9-tetrahydro-1-H-pyrrolo[3.2-h]naphthalene-2,3-dione-3-O-(4-hydroxybutyric acid-2-yl)oxime (Compound O-2)
5-(6-chloropyrid-3-yl)-6,7,8,9-tetrahydro-1-H-pyrrolo[3.2-h]naphthalene-2,3-dione-3-O-(4-hydroxybutyric acid-2-yl)oxime (Compound O-3)

5-(5-chloropyrimid-2-yl)-6,7,8,9-tetrahydro-1-H-pyrrolo [3.2-h]naphthalene-2,3-dione-3-O-(4-hydroxybutyric acid-2-yl)oxime (Compound O-4)

5-(2-chloropyrimid-5-yl)-6,7,8,9-tetrahydro-1-H-pyrrolo [3.2-h]naphthalene-2,3-dione-3-O-(4-hydroxybutyric acid-2-yl)oxime (Compound O-5)

5-(6-chloropyridazin-3-yl)-6,7,8,9-tetrahydro-1-H-pyrrolo [3.2-h]naphthalene-2,3-dione-3-O-(4-hydroxybutyric acid-2-yl)oxime (Compound O-6)

5-(5-chloropyrazin-2-yl)-6,7,8,9-tetrahydro-1-H-pyrrolo [3.2-h]naphthalene-2,3-dione-3-O-(4-hydroxybutyric acid-2-yl)oxime (Compound O-7)

5-(5-chlorothien-2-yl)-6,7,8,9-tetrahydro-1-H-pyrrolo[3.2-h]naphthalene-2,3-dione-3-O-(4-hydroxybutyric acid-2-yl)oxime (Compound O-8)

5-(5-chloro-1,1-dioxy-thien-2-yl)-6,7,8,9-tetrahydro-1-H-pyrrolo[3.2-h]naphthalene-2,3-dione-3-O-(4-hydroxybutyric acid-2-yl)oxime (Compound O-9)

5-(5-chlorothiazol-2-yl)-6,7,8,9-tetrahydro-1-H-pyrrolo [3.2-h]naphthalene-2,3-dione-3-O-(4-hydroxybutyric acid-2-yl)oxime (Compound O-10)

5-(2-chlorothiazol-5-yl)-6,7,8,9-tetrahydro-1-H-pyrrolo [3.2-h]naphthalene-2,3-dione-3-O-(4-hydroxybutyric acid-2-yl)oxime (Compound O-11)

Example 2

Survival of Differentiated PC12 Cells in Serum-free Medium

In this experiment the protective effect of the compounds on the survival of the pheochromocytoma cell line PC12 deprived of other survival factors were assessed following differentiation of the cells to a neuron-like phenotype.

Method

Cells were seeded in collagen coated 96 well plates at a cell density of 8,000/cm$^2$ in DMEM with 7.5% Foetal Calf Serum (FCS), 7.5% Donor Horse Serum (DHS) and 2 nM NGF and cultured for 6 days. The medium was then changed to DMEM without serum supplemented with the compound in the indicated concentrations. As a positive control, parallel wells receiving serum-free DMEM without addition of vehicle or 3 nM NGF were included.

After 4 days of incubation, cell viability was evaluated by using MTS (3-(4,5-dimethylthiazol-2-yl)-5-(3-carboxymethoxyphenyl)-2-(4-sulfonyl)$_2$H-tetrazolium) which is reduced by metabolically active cells. Data are expressed as % of the response seen with 3 nM NGF corrected for residual MTS reduction activity in the parallel serum-free cultures ("% of NGF control").

The results of this experiment are presented in Table 1 below.

TABLE 1

Survival Effects on Differentiated PC12 Cells in Serum-free Medium (% of 3 nM NGF)

| Concentration (μM) | Compound G-1 | Compound G-2 | Compound G-3 |
|---|---|---|---|
| 0.1 | 11.09 ± 1.42 | 7.77 ± 1.86 | −0.34 ± 1.59 |
| 0.2 | 12.78 ± 2.01 | 16.58 ± 4.36 | 23.83 ± 3.61 |
| 0.5 | 28.62 ± 1.77 | 17.30 ± 4.43 | 28.20 ± 2.55 |
| 0.75 | 32.05 ± 3.36 | 23.54 ± 1.60 | 30.66 ± 3.83 |
| 1 | 52.60 ± 3.40 | 27.63 ± 6.91 | 36.11 ± 3.02 |
| 2 | 60.47 ± 2.26 | 33.31 ± 5.22 | 41.53 ± 3.00 |
| 5 | 74.85 ± 4.67 | 50.25 ± 4.28 | 49.63 ± 4.67 |
| 7.5 | 62.08 ± 3.70 | 54.83 ± 4.37 | 67.60 ± 5.54 |
| 10 | 63.80 ± 4.09 | 74.66 ± 5.70 | 72.23 ± 4.34 |

Table 1 shows the effect of the compounds Compound G-1, Compound G-2 and Compound G-3 on PC12 cell survival in serum-free medium measuring viability as reduction of MTS. All of the three compounds show a dose-dependent rescue of PC12 cells in serum-free medium. Maximal survival effects of the compounds, which is 70-75% of the effect of 3 nM NGF, are seen at concentrations between 5-10 μM of the compounds.

Example 3

Stimulation of Neurite Outgrowth in PC12 Cells

In this experiment the ability of the compounds to potentiate NGF-induced neurite outgrowth in PC12 cells was assessed.

Method

PC12 cells were seeded in tissue culture plates coated with collagen at a cell density of 15,000/cm$^2$ in DMEM with 7.5% FCS and 7.5% DHS. Next day the medium was changed to medium supplemented with the NS compound in the absence or presence of NGF.

Two days after the medium change, cells were fixed in 4% paraformaldehyde and stained for neurofilament. Cells were fixed by in tissue culture plates by incubation in 4% paraformaldehyde in PBS followed permeabilization in 0.05% Triton-X100 in the presence of 10% DHS to block non-specific binding sites. After washing, the plates were incubated with anti-neurofilament (NF) antibody (clone RT97) from Boehringer diluted 1:200 in 0.05% Triton-X100/10% DHS followed by incubation with biotinylated anti-mouse immunoglobulin RPN1001 (Amersham) diluted 1:200. NF-immunoreactive cells were stained using the ABC-complex/HRP kit K0355 (DAKO) and 3,3-diaminobenzidine tetrahydrochloride (DAB) as substrate.

Estimation of total cell number per well, as well as the total neurite length was done using unbiasedly 2D stereology (CAST-grid system connected to a Olympus BH-2 microscope).

The results of this experiment are presented in FIG. 1. From this figure it appears that Compound G-1 alone (1 and 3 μM) shows some effect on neurite outgrowth in PC12 cells and significantly potentiate NGF-induced neurite outgrowth.

Example 4

Survival of Embryonic Rat Dopaminergic Neurons

In this experiment the effect of Compound G-1 on the survival of dopaminergic neurons in dissociated cultures established from rat E14 ventral mesencephali (VM) is assessed.

Method

Embryonic rat brains (Wistar; E14) were isolated under sterile conditions placed in chilled Gey's balanced salt solution (GIBCO) with glucose (6.5 mg/ml).

The ventral mesencephali were dissected out, cut into small tissue pieces, placed in Neurobasal medium with B27 supplement and gently pressed through a 80 μm Nitex filter. The cells were counted using a hemocytometer and plated in a 6 well multi-dish at a density of approximately 2.0×10$^6$ cells/well. Culture dishes were pre-coated with poly-D-lysine.

After 1 hour, the medium was removed and fresh medium added (1.5 ml/well). One group of cultures was treated chronically with Compound G-1 at a concentration of 1 μM. Untreated cultures served as controls. The medium was changed every other day and antimitotics and antibiotics were not used at any stage.

After 7 days in culture, cultures were then immunostained for tyrosine hydroxylase (TH). Briefly, the cells were washed in 0.05M tris-buffered saline (TBS, pH 7.4) containing 1% Triton X-100 for 3×15 minutes and incubated with 10% foetal bovine serum (FBS, Life Technologies) in TBS for 30 minutes. The cells were then incubated for 24 hours at 4° C. with monoclonal mouse anti-TH antibody (Boehringer Mannheim) diluted 1:600 in TBS with 10% FBS. After rinsing in TBS with 1% Triton X-100 for 3×15 minutes, cells were incubated for 60 minutes with biotinylated anti-mouse IgG antibody (Amersham) diluted 1:200 in TBS with 10% FBS. The cells were then washed in TBS with 1% Triton X-100 (3×15 minutes) and incubated for 60 minutes with streptavidine-peroxidase (Dako) diluted 1:200 in TBS with 10% FBS. After washing in TBS (3×15 minutes), bound antibody was visualised by treatment with 0.05% 3,3-diaminobenzidine (Sigma) in TBS containing 0.01% $H_2O_2$. TH-immunoreactive (ir) cells were counted manually.

Figure 2:
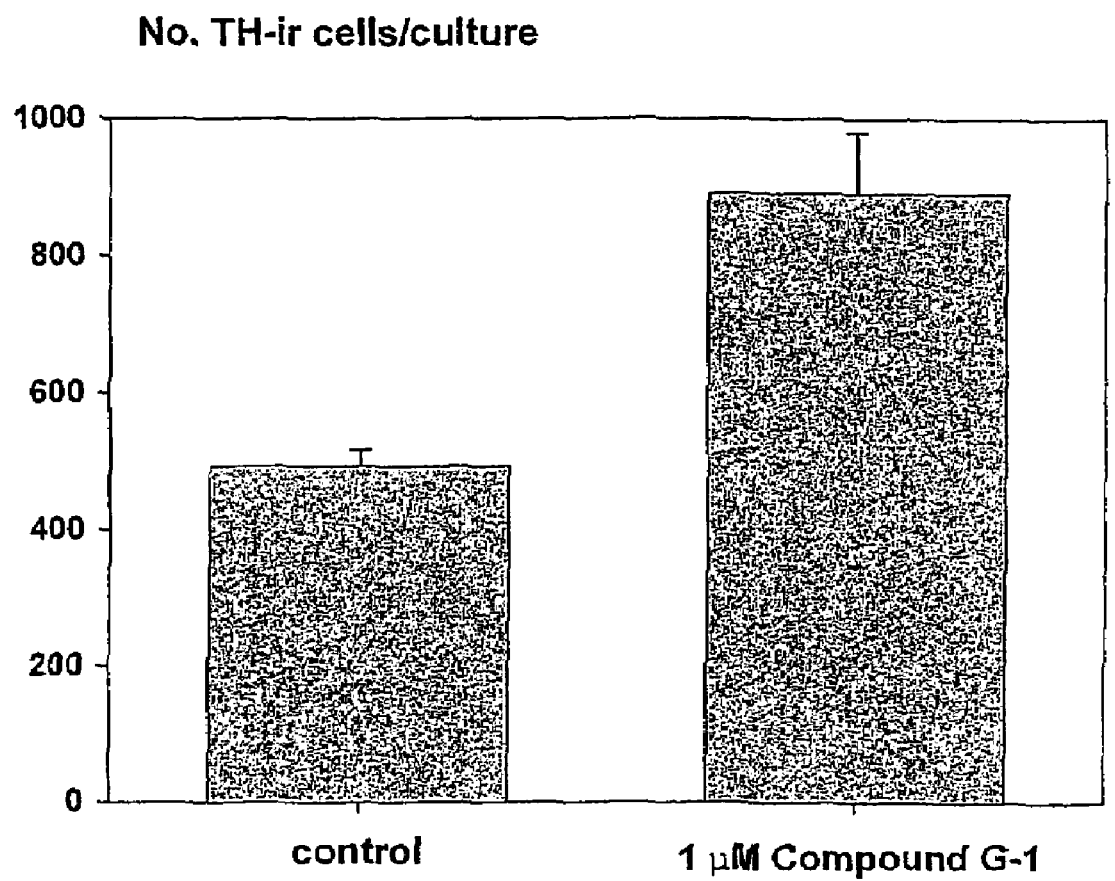
FIG. 2 illustrates the effect of Compound G-1 on the number TH-ir present in cultures from E14 rat VM grown for 7 days in culture. In this experiment, 81% more TH-immunoreactive cells were found in cultures treated with 1 µM Compound G-1 compared to untreated control cultures (p<0.016 Mann-Whitney test) indicating that the compound has a survival effect on this neuronal population in rats.

The results of this experiment are presented in FIG. 2. From this figure it appears that 81% more TH-immunoreactive cells were found in cultures treated with 1 μM Compound G-1 compared to untreated control cultures ($p<0.016$ Mann-Whitney test) indicating that the compound has a survival effect on this neuronal population in rats.

Example 5

Survival of Dopaminergic Neurons from E28 Pig Ventral Mesencephali

In this experiment the effect of Compound G-1 on the survival of dopaminergic neurons in organotypic slice cultures established from pig E28 ventral mesencephali was assessed.

Method

Ventral mesencephali (VM) were isolated from porcine embryos (E28) under sterile conditions, chopped into 400 μm slices and placed in chilled Gey's balanced salt solution (GIBCO) with glucose (6.5 mg/ml). The tissue slices were cultured by the interface culture method, originally developed by Stoppini et al. [L. Stoppini, P. A. Buchs, D. Muller: A simple method for organotypic cultures of nervous tissue; *J. Neurosci. Methods* 1991 37 173-182].

In brief, slices were placed on semiporous membranes (Millipore, 0.3 μm; 4 slices/membrane) placed as inserts in 6-well plates (Costar) with serum containing medium (Gibco BRL). Each well contained 1 ml medium (50% Optimem, 25% horse serum, 25% Hank's balanced salt solution (all GIBCO)) supplemented with D-glucose to a final concentration of 25 mM.

At day 3, the medium was replaced by defined serum-free medium (Neurobasal medium with B27 supplement from Life Technologies). The cultures were grown in an incubator with 5% $CO_2$ at 36° C. for 21 days after which the sections were immunostained for TH as described in Example 4. One group of slice cultures was treated chronically with Compound G-1 at a concentration of 1 μM. Untreated cultures served as controls. The medium was changed twice a week and antimitotics and antibiotics were not used at any stage.

Quantification of TH-ir neurons was performed on coded slides (to allow analysis by experiments "blinded" to sample identity) using an Olympus C.A.S.T. Grid system (version 1.10; Olympus, Albertslund, Denmark) composed of an Olympus BX50 microscope and an x-y-z step motor stage run by a computer. The area of the culture slice was delineated and a counting frame was randomly placed to mark the first area to be sampled. The frame was then systematically moved through the sections and the TH-ir cells counted.

Figure 3:
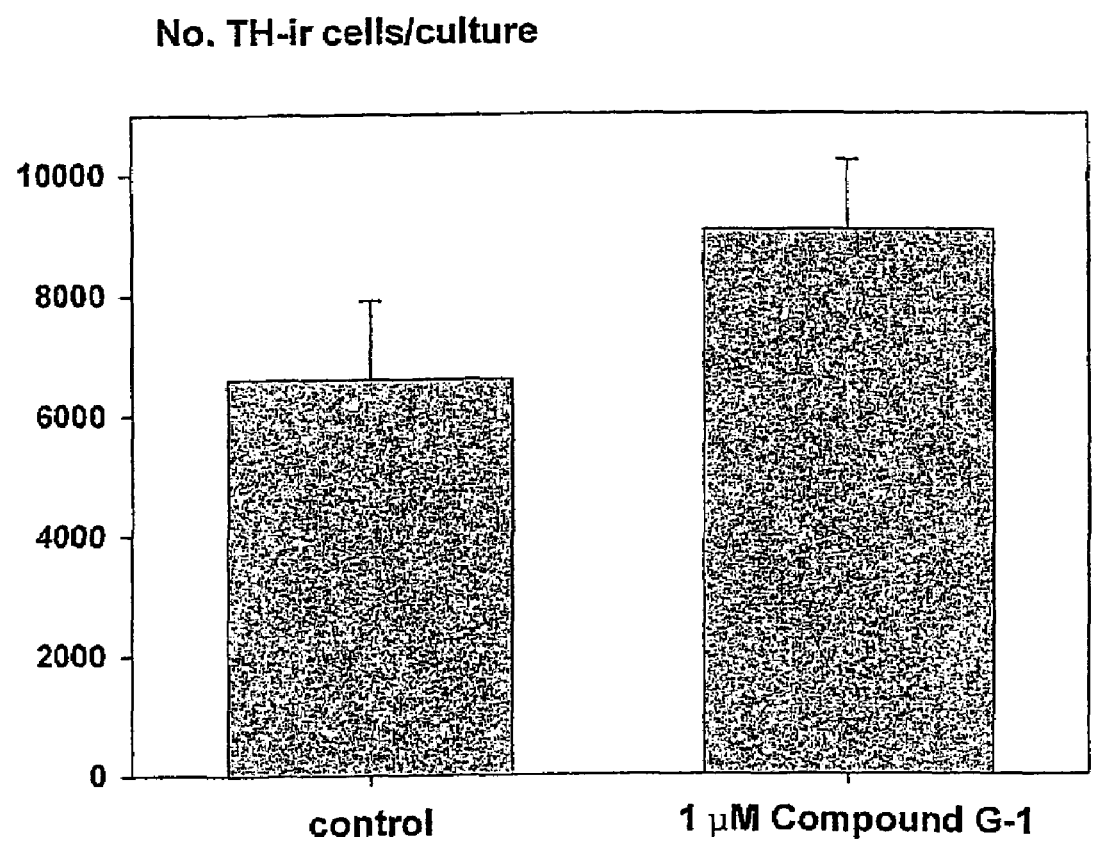
FIG. 3 illustrates the effect of Compound G-1 on the number of TH-IR in slice cultures grown in vitro for 21 days. In this experiment, 37% more TH-immunoreactive cells were found in cultures treated with 1 µM Compound G-1 compared to untreated control cultures (p<0.038 Mann-Whitney test) indicating that the compound has a survival effect on this neuronal population in pigs.

The results of this experiment are presented in FIG. 3. From this figure it appears that 37% more TH-immunoreactive cells were found in cultures treated with 1 μM Compound G-1 compared to untreated control cultures ($p<0.038$ Mann-Whitney test) indicating that the compound has a survival effect on this neuronal population in pigs.

Example 6

NGF Signal Transduction in PC12 Cells

In this experiment the effect of Compound G-1 on NGF-induced phosphorylation of the ERKs and the Akt kinase was assessed.

Method

Approximately 200,000 PC12 cells were plated in a 24 well plate in DMEM with 7.5% FCS and 7.5% DHS and incubated ON. The next day NGF and Compound G-1 were added to the cells and they were incubated for 24 hours after which the cells were harvested in 2×Laemmli sample buffer.

Total cell lysate was electrophoresed on 8-18% gradient SDS gels which were electroblotted to PVDF membranes. Phosphorylated ERK1 and ERK2 were immunodetected by using mouse anti-Phospho-p44/p42 MAP kinase E10 mAb (New England Biolabs #9106) and HRP-linked anti-mouse antibody. Phosphorylated Akt kinase was immunodetected by using rabbit phospho-specific Akt (Ser473) antibody (New England Biolabs # 9271) and HRP-linked anti-rabbit antibody. Bands were detected by chemilumininescence using the ECL system (Amersham).

Figure 4:
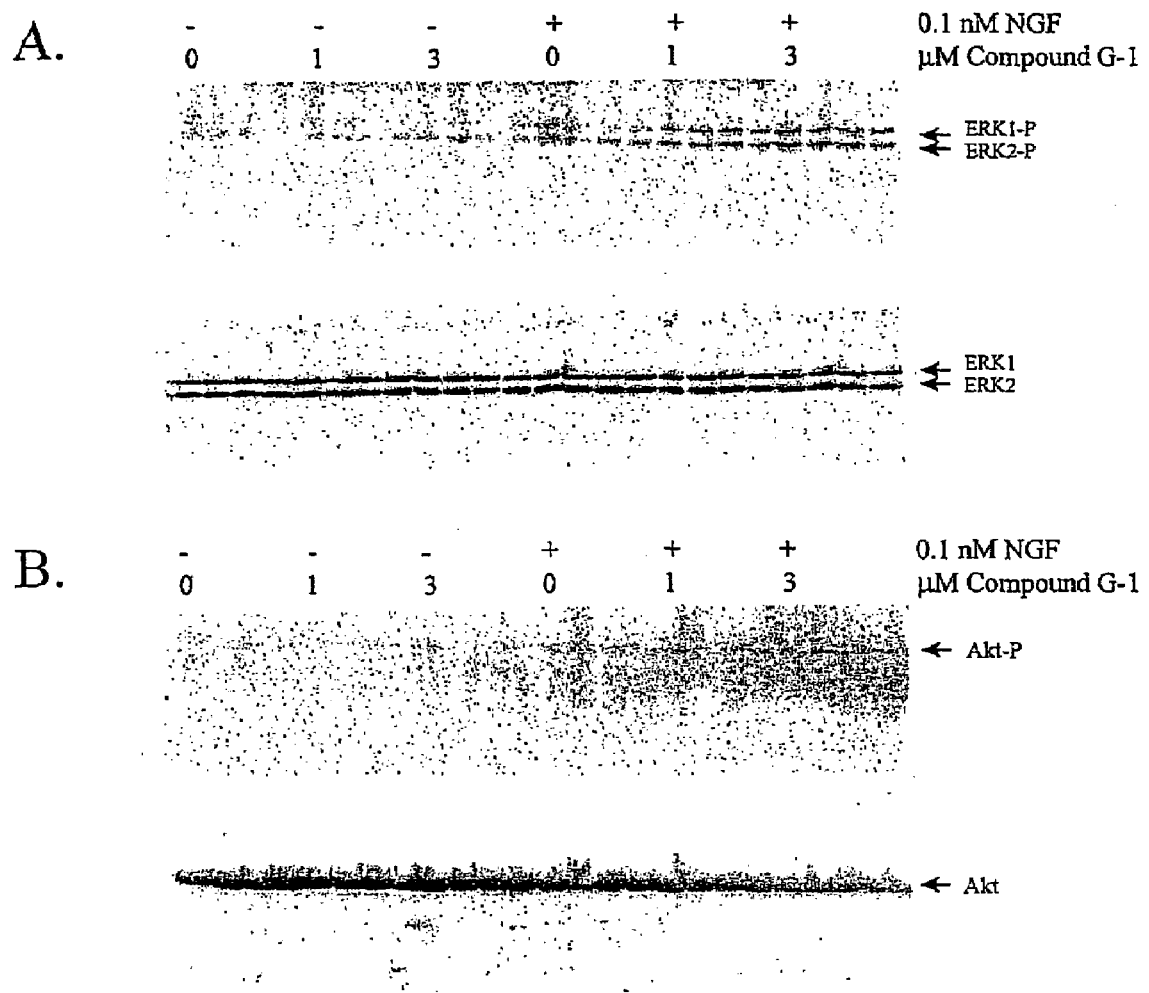
FIG. 4 (A and B) illustrates the effect of 1-3 µM Compound G-1 on NGF-induced phosphorylation of the ERKs and the Akt kinase. In these experiments the ability of µM concentrations of Compound G-1 to potentiate NGF-induced phosphorylation of kinases (the ERKs and the Akt kinase) important for signal transduction is seen.

The results of this experiment are presented in FIGS. 4A and 4B. From these figures the ability of μM concentrations of Compound G-1 to potentiate NGF-induced phosphorylation of kinases (the ERKs and the Akt kinase) important for signal transduction is seen.

Example 7

Transient Global Ischaemia in Gerbils

In this experiment, the neuroprotective effect of Compound G-2 was assessed in an animal model of transient global ischaemia.

Method

Gerbils were anaesthetised with halothane, right and left carotid arteries located and occluded for 4 minutes. Animals were kept at normal body temperature before and after the operation using heating lamps. During the operation, the gerbils were placed on heating pads, the body temperature was controlled and maintained at 37±0.5° C. Animals received 30 mg/kg Compound G-2 administrated intraperitoneally 15 minutes after the ischaemic insult and the following day.

Four days later, the animals were sacrificed, brains removed and cooled to −70° C. Thereafter, the brains were sectioned in 20 μm thick sections of which 5-7 with hippocampal tissue were selected and stained with hematoxylin-eosin.

Figure 5:
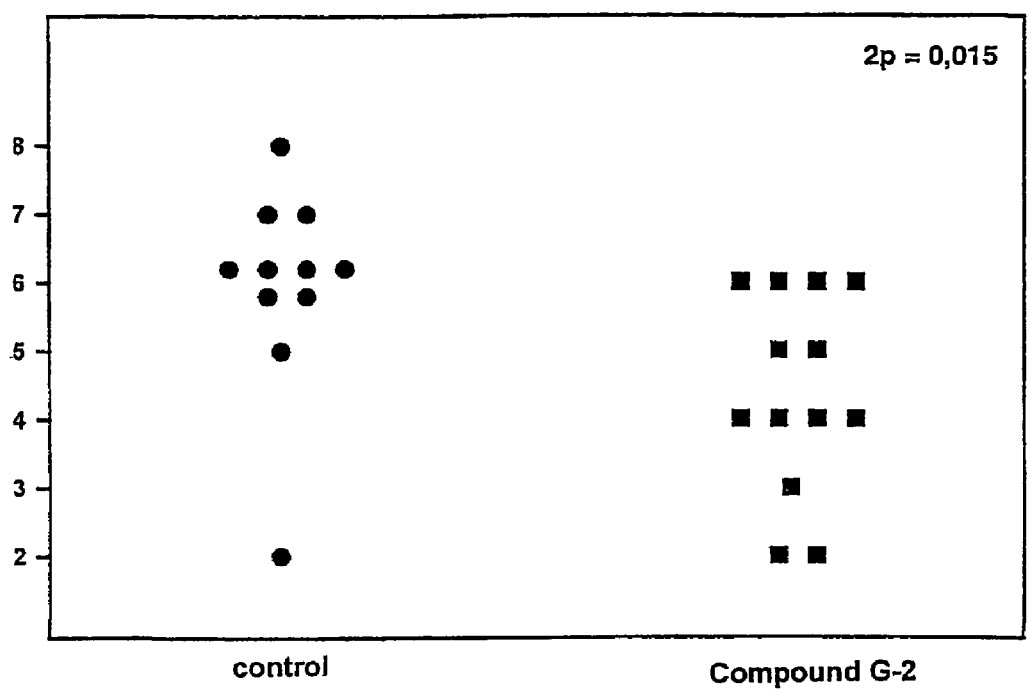
FIG. 5 illustrates the effect of Compound G-2 on the hippocampal damage after 4 minutes of transient global ischaemia in a gerbil model. The degree of hippocampal damage was categorised into one of four groups: Group 1: no damage in the $CA_1$-layer; Group 2: the $CA_1$-layer partly damaged; Group 3: the $CA_1$-layer completely damaged; and Group 4: damage in more then just the $CA_1$-layer. The total ischaemia score was obtained as the sum of scores in the right- and left hemisphere. Kendall's tau test was used for statistic evaluation. Most (≈80%) of the untreated animals show total damage in the hippocampal $CA_1$-layer. In contrast in many animals (≈50%) receiving with Compound G-2 after the ischaemic insult (2×30 mg/kg ip.), no or only partially damage in the $CA_1$ neurons of the hippocampus is seen.

The results of this experiment are presented in FIG. 5.

The degree of hippocampal damage was categorised into one of four groups:

Group 1: no damage in the $CA_1$-layer;
Group 2: the $CA_1$-layer partly damaged;
Group 3: the $CA_1$-layer completely damaged; and Group 4: damage in more then just the $CA_1$-layer. The total ischaemia score was obtained as the sum of scores in the right- and left hemisphere. Kendall's tau test was used for statistic evaluation.

From this figure it appears that most (≈80%) of the untreated animals show total damage in the hippocampal $CA_1$-layer. In contrast in many animals (≈50%) receiving with Compound G-2 after the ischaemic insult (2×30 mg/kg ip.), no or only partially damage in the $CA_1$ neurons of the hippocampus is seen.

Example 8

Stimulation of CREB Phosphorylation in Undifferentiated PC12 Cells

The cyclic AMP-responsive element binding protein (CREB) is a post-translationally activated transcription factor that has been implicated in numerous neuronal functions including cell survival, differentiation and neurotransmission. In this experiment the effect of Compound G-1 on CREB phosphorylation was assessed.

Method

Approximately 7.5×10⁵ PC12 cells per well were plated in collagen coated 6-well plates in DMEM with 0.75% FCS and 0.75% DHS and incubated for 48 hours. Cells were then further starved for 2 hours in serum free DMEM before stimulation with the indicated compounds for 5, 10 or 20 minutes. Cells were harvested in 1× heated sample buffer (2% SDS, 400 mM Tris, pH 8.0, 10 mM DTT and 0.25 mM $Na_3VO_4$) and the cell lysates were electrophoresed on 8-18% gradient SDS gels, which were electroblotted to PVDF membranes.

Phosphorylated CREB were immunodetected by using rabbit anti-Phospho-CREB (UpState Biotechnology #06-519) followed by HRP-linked anti-rabbit antibody (Amersham Life Science #NA 934). Bands were detected by chemilumininescence using the ECL system (Amersham).

Figure 6:
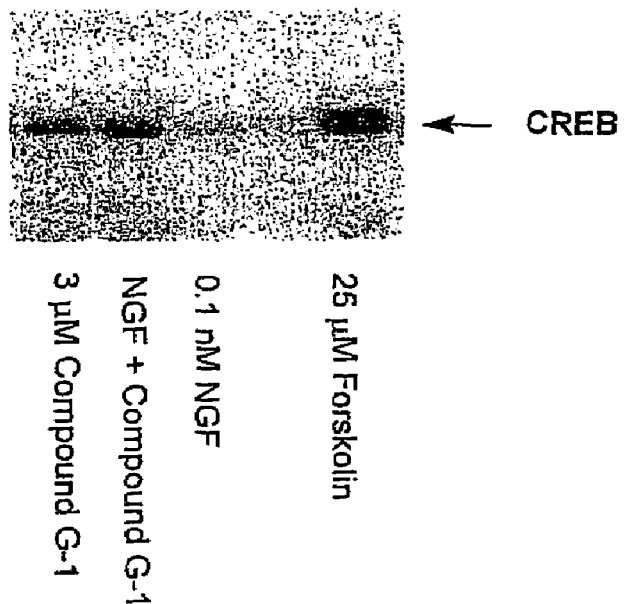
FIG. 6 illustrates the effect of 20 minutes stimulation with 3 mM Compound G-1 on CREB phosphorylation in undifferentiated PC12 cells, alone or added together with a suboptimal NGF concentration (0.1 nM). Forskolin was added as a positive control, as it is known to stimulate CREB phosphorylation via elevation of intracellular cAMP and activation of PKA. Compound G-1 was shown to stimulate CREB phos-

The results of this experiment are presented in FIG. 6. From this figure it appears that Compound G-1 stimulates CREB phosphorylation compared to unstimulated cells as well as cells stimulated with 0.1 nM NGF at time points from 5 to 20 minutes.

An additive effect of NGF and Compound G-1 was seen after 5 minutes stimulation (not shown).

The invention claimed is:
1. An having the general formula (IV):

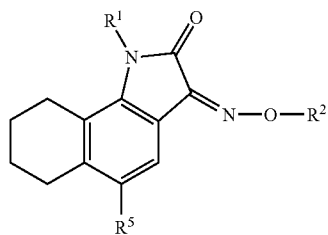

(IV)

or a pharmaceutically acceptable salt thereof
wherein
$R^1$ represents hydrogen or an alkyl group;
$R^2$ represents an alkyl group substituted with one or more hydroxyl or carboxyl groups; and
$R^5$ represents a phenyl group, a benzyl group, or a 5- or 6-membered monocyclic heterocyclic group, which groups may optionally be substituted one or more times with halogen, $CF_3$, —$OCF_3$, $NO_2$, amino, aminosulfonyl, alkyl, alkoxy, alkoxycarbonyl, or phenyl.

2. The of claim 1, wherein $R^1$ represents hydrogen, or a pharmaceutically acceptable salt thereof.

3. The of claim 1, wherein $R^2$ represents a $C_{3-6}$-alkyl substituted with hydroxyl and carboxyl, or a pharmaceutically acceptable salt thereof.

4. The of claim 1, wherein $R^5$ represents a phenyl group, which group may optionally be substituted one or more times with halogen, $CF_3$, $NO_2$, amino, alkyl, alkoxy, or phenyl, or a pharmaceutically acceptable salt thereof.

5. The of claim 1, wherein $R^5$ represents phenyl substituted in the 4-position with halogen, $CF_3$, $NO_2$, amino, alkyl, or alkoxy, or a pharmaceutically acceptable salt thereof.

6. The of claim 1, being
  5-(4-chlorophenyl)-6,7,8,9-tetrahydro-1-H-pyrrolo[3.2-h]naphthalene-2,3-dione-3-O-(4-hydroxybutyric acid-2-yl)oxime;
  5-(5-chloropyrid-2-yl)-6,7,8,9-tetrahydro-1-H-pyrrolo[3.2-h]naphthalene-2,3-dione-3-O-(4-hydroxybutyric acid-2-yt)oxime;
  5-(6-chloropyrid-3-yl)-6,7,8,9-tetrahydro-1-H-pyrrolo[3.2-h]naphthalene-2,3-dione-3-O-(4-hydroxybutyric acid-2-yl)oxime;
  5-(5-chioropyrimid-2-yl)-6,7,8,9-tetrahydro-1-H-pyrrolo[3.2-h]naphthalene-2,3 -dione-3-O-(4-hydroxybutyric acid-2-yl)oxime;
  5-(2-chloropyrimid-5-yl)-6,7,8,9-tetraihydro-1-H-pyrrolo[3.2-h]naphthalene-2,3-dione-3-O-(4-hydroxybutyric acid-2-yl)oxime;
  5-(6-chloropyridazin-3-yl)-6,7,8,9-tetrahydro-1-H-pyrrolo[3.2-h]naphthalene-2,3-dione-3-O-(4-hydroxybutyric acid-2-yl)oxime;
  5-(5-chloropyrazin-2-yl)-6,7,8,9-tetrahydro-1-H-pyrrolo[3.2-h]naphthalene-2,3-dione-3-O-(4-hydroxybutyric acid-2-yl)oxime;
  5-(5-chlorothien-2-yl)-6,7,8,9-tetrahydro- 1-H-pyrrolo[3.2-h]naphthalene-2,3-dione-3-O-(4-hydroxybutyric acid-2-yl)oxime;
  5-(5-chloro-1,1-dioxy-thien-2-yl)-6,7,8,9-tetrahydro-1-H-pyrrolo[3.2-h]naphthalene-2,3-dione-3-O-(4-hydroxybutyric acid-2-yl)oxime;
  5-(5-chlorothiazol-2-yl)-6,7,8,9-tetrahydro-1-H-pyrrolo[3.2-h]naphthalene-2,3-dione-3-O-(4-hydroxybutyric acid-2-yl)oxime;
  5-(2-chlorothiazol-5-yl)-6,7,8,9-tetrahydro- 1-H-pyrrolo[3.2-h]naphthalene-2,3-dione-3-O-(4-hydroxybutyric acid-2-yl)oxime; or
  a pharmaceutically acceptable salt thereof.

7. The of claim 6, which is
  5-(4-chlorophenyl)-6,7,8,9-tetrahydro-1-H-pyrrolo[3.2-h]naphthalene-2,3-dione-3-O-(4-hydroxybutyric acid-2-yl)oxime, or a pharmaceutically acceptable salt thereof.

8. A pharmaceutical composition comprising a therapeutically-effective amount of a compound according to claim 1, or a pharmaceutically-acceptable salt thereof, together with at least one pharmaceutically-acceptable carrier or diluent.

* * * * *